(12) United States Patent
Siegel et al.

(10) Patent No.: US 9,023,627 B2
(45) Date of Patent: May 5, 2015

(54) SYSTEMS AND METHODS FOR BIOTRANSFORMATION OF CARBON DIOXIDE INTO HIGHER CARBON COMPOUNDS

(75) Inventors: Justin Siegel, Davis, CA (US); David Baker, Seattle, WA (US); Amanda Lee Smith, Seattle, WA (US); Mary E. Lidstrom, Seattle, WA (US); Catherine Louw, Bellevue, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 0 days.

(21) Appl. No.: 13/823,941

(22) PCT Filed: Sep. 15, 2011

(86) PCT No.: PCT/US2011/051847
§ 371 (c)(1),
(2), (4) Date: Mar. 15, 2013

(87) PCT Pub. No.: WO2012/037413
PCT Pub. Date: Mar. 22, 2012

(65) Prior Publication Data
US 2013/0196359 A1 Aug. 1, 2013

Related U.S. Application Data

(60) Provisional application No. 61/383,249, filed on Sep. 15, 2010.

(51) Int. Cl.
*C12N 9/88* (2006.01)
*C12P 7/24* (2006.01)
*C12P 7/26* (2006.01)

(52) U.S. Cl.
CPC ... *C12N 9/88* (2013.01); *C12P 7/24* (2013.01); *C12P 7/26* (2013.01); *C12Y 401/02038* (2013.01)

(58) Field of Classification Search
None
See application file for complete search history.

(56) References Cited

U.S. PATENT DOCUMENTS

| | | |
|---|---|---|
| 5,329,023 A | 7/1994 | Brussee |
| 2004/0014182 A1 | 1/2004 | Pohl |
| 2004/0063175 A1 | 4/2004 | Abraham |
| 2005/0106305 A1 | 5/2005 | Abraham |
| 2005/0112260 A1 | 5/2005 | Abraham |
| 2005/0170041 A1 | 8/2005 | Abraham |
| 2005/0221455 A1 | 10/2005 | McFarlan |
| 2005/0244937 A1 | 11/2005 | Abraham |
| 2009/0117625 A1 | 5/2009 | Abraham |
| 2009/0130285 A1 | 5/2009 | Abraham |
| 2009/0139134 A1 | 6/2009 | Yoshikuni |
| 2009/0155873 A1 | 6/2009 | Kashiyama |
| 2009/0203089 A1 | 8/2009 | Kashiyama |
| 2010/0086981 A1 | 4/2010 | LaTouf |

FOREIGN PATENT DOCUMENTS

| | | |
|---|---|---|
| WO | 2005/016022 A1 | 2/2005 |
| WO | 2006/087266 A1 | 8/2006 |
| WO | 2009/046370 A2 | 4/2009 |
| WO | 2009/046375 A2 | 4/2009 |
| WO | 2009/097346 A2 | 8/2009 |

OTHER PUBLICATIONS

By Kneen et al. Biochimica et Biophysica Acta 1753 (2), 263-271.*
Yan, R.-T., and J.-S. Chen, "Coenzyme A—Acylating Aldehyde Dehydrogenase From *Clostridium beijerinckii* NRRL B592," Applied and Environmental Microbiology 56(9):2591-2599, Sep. 1990.
Yin, Y., and J.F. Kirsch, "Identification of Functional Paralog Shift Mutations: Conversion of *Escherichia coli* Malate Dehydrogenase to a Lactate Dehydrogenase," Proceedings of the National Academy of Sciences of the United States of America (PNAS) 104(44):17353-17357, Oct. 2007.
Yoshikuni, Y., and J.D. Keasling, "Pathway Engineering by Designed Divergent Evolution," Current Opinion in Chemical Biology 11(2):233-239, Apr. 2007.
Yoshikuni, Y., et al., "Designed Divergent Evolution of Enzyme Function," Nature 440(7087):1078-1082, Apr. 2006.
Zanghellini, A., et al., "New Algorithms and an In Silico Benchmark for Computational Enzyme Design," Protein Science 15(12):2785-2794, Dec. 2006.
Zavrel, M., et al., "Mechanistic Kinetic Model for Symmetric Carboligations Using Benzaldehyde Lyase," Biotechnology and Bioengineering 101(1):27-38, Sep. 2008 (author's proof).
Kuhlman, B., and D. Baker, "Native Protein Sequences Are Close to Optimal for Their Structures," Proceedings of the National Academy of Sciences of the United States of America (PNAS) 97(19):10383-10388, Sep. 2000.
Kumari, S., et al., "Cloning, Characterization, and Functional Expression of acs, the Gene Which Encodes Acetyl Coenzyme A Synthetase in *Escherichia coli*," Journal of Bacteriology 177(10):2878-2886, May 1995.
Kunkel, T.A., "Rapid and Efficient Site-Specific Mutagenesis Without Phenotypic Selection," Proceedings of the National Academy of Sciences of the United States of America (PNAS) 82(2):488-492, Jan. 1985.
Lazaridis, T., and M. Karplus, "Effective Energy Function for Proteins in Solution," Proteins: Structure, Function, and Genetics 35(2):133-152, May 1999.
Lee, S.-J., et al., "Coupled Expression of MhpE Aldolase and MhpF Dehydrogenase in *Escherichia coli*," Biochemical and Biophysical Research Communications 346(3):1009-1015, Aug. 2006.
Lennard-Jones, J.E., "Cohesion," Proceedings of the Physical Society 43 (Pt. 5)(240):461-482, Sep. 1931.

(Continued)

*Primary Examiner* — Nashaat Nashed
(74) *Attorney, Agent, or Firm* — Christensen O'Connor Johnson Kindness PLLC

(57) ABSTRACT

Systems, compounds and methods for the conversion of C1 carbon compounds to higher carbon compounds useful for the generation of commodity compounds.

19 Claims, 5 Drawing Sheets

(56) References Cited

OTHER PUBLICATIONS

Li, H., and C. Oloman, "The Electro-Reduction of Carbon Dioxide in a Continuous Reactor," Journal of Applied Electrochemistry 35(10):955-965, Oct. 2005.

Lidstrom, M.E., and D.I. Stirling, "Methylotrophs: Genetics and Commercial Applications," Annual Review of Microbiology 44:27-58, Oct. 1990.

Lin, H., et al., "Acetyl-CoA Synthetase Overexpression in *Escherichia coli* Demonstrates More Efficient Acetate Assimilation and Lower Acetate Accumulation: A Potential Tool in Metabolic Engineering," Applied Genetics and Molecular Biotechnology 71(6):870-874, Aug. 2006.

Mast, N., "Broad Substrate Specificity of Human Cytochrome P450 46A1 Which Initiates Cholesterol Degradation in the Brain," Biochemistry 42(48):14284-14292, Dec. 2003.

Matsumoto, T., et al., "Selective Formation of Triose From Formaldehyde Catalyzed by Thiazolium Salt," Journal of the American Chemical Society 106(17):4829-4832, Aug. 1984.

Meiler, J., and D. Baker, "Rosettaligand: Protein—Small Molecule Docking With Full Side-Chain Flexibility," Proteins: Structure, Function, and Bioinformatics 65(3):538-548, Nov. 2006.

Michaelis, L., and M.L. Menten, "Die Kinetik der Invertinwirkung," Biochemistry Zeitung 49:333-369, 1913, and English translation by K.A. Johnson and R.S. Goody, "The Original Michaelis Constant: Translation of the 1913 Michaelis-Menten Paper," Biochemistry 50(39):8264-8269, Oct. 2011.

Michel, C., et al., "Adenosylcobalamin and Cob(II)alamin as Prosthetic Groups of 2-Methyleneglutarate Mutase From *Clostridium barkeri*," European Journal of Biochemistry/FEBS 205(2):767-773, Apr. 1992.

Nakamura, C.E., and G.M. Whited, "Metabolic Engineering for the Microbial Production of 1,3-Propanediol," Current Opinion in Biotechnology 14(5):454-459, Oct. 2003.

Obert, R., and B.C. Dave, "Enzymatic Conversion of Carbon Dioxide to Methanol: Enhanced Methanol Production in Silica Sol—Gel Matrices," Journal of the American Chemical Society 121(51):12192-12193, Dec. 1999.

Page, M.I., and W.P. Jencks, "Entropic Contributions to Rate Accelerations in Enzymic and Intramolecular Reactions and the Chelate Effect," Proceedings of the National Academy of Sciences of the United States of America (PNAS) 68(8):1678-1683, Aug. 1971.

Park, H.-S., et al., "Design and Evolution of New Catalytic Activity With an Existing Protein Scaffold," Science 311(5760):535-538, Jan. 2006.

Pauling, L., "Nature of Forces Between Large Molecules of Biological Interest," Nature 161(4097):707-709, May 1948.

Pauling, L., "Molecular Architecture and Biological Reactions," Chemical and Engineering News 24(10):1375-1377, May 1946.

Payen, A., and J.-F. Persoz, "Mémoire sur la Diastase, les Principaux Produits de ses Réactions, et Leurs Applications aux Arts Industriels (Memoir on Diastase, the Principal Products of Its Reactions, and Their Applications to the Industrial Arts)," Annales de Chimie et de Physique, 1833, 2nd Series, vol. 53, pp. 73-92.

Porath, J., "Immobilized Metal Ion Affinity Chromatography," Protein Expression and Purification 3(4):263-281, Aug. 1992.

Röthlisberger, D., et al., "Kemp Elimination Catalysts by Computational Enzyme Design," Nature 453(7192):190-195, May 2008.

Schenk, G., et al., "Properties and Functions of the Thiamin Diphosphate Dependent Enzyme Transketolase," International Journal of Biochemistry & Cell Biology 30(12):1297-1318, Dec. 1998.

Seelig, B., and J.W. Szostak, "Selection and Evolution of Enzymes From a Partially Randomized Non-Catalytic Scaffold," Nature 448(7155):828-831, Aug. 2007.

Shah, K., et al., "Engineering Unnatural Nucleotide Specificity for Rous Sarcoma Virus Tyrosine Kinase to Uniquely Label Its Direct Substrates," Proceedings of the National Academy of Sciences of the United States of America (PNAS) 94(8):3565-3570, Apr. 1997.

Shapiro, A.L., et al., "Molecular Weight Estimation of Polypeptide Chains by Electrophoresis in SDS-Polyacrylamide Gels," Biochemical and Biophysical Research Communications 28(5):815-820, Sep. 1967.

Simonov, A.N., et al., "The Nature of Autocatalysis in the Butlerov Reaction," Kinetics and Catalysis 48(2):245-254, Mar. 2007.

Simons, K.T., et al., "Improved Recognition of Native-Like Protein Structures Using a Combination of Sequence-Dependent and Sequence-Independent Features of Proteins," Proteins 34(1):82-95, Jan. 1999.

Stemmer, W.P.C., "Rapid Evolution of a Protein In Vitro by DNA Shuffling," Nature 370(6488):389-391, Aug. 1994.

Studier, F.W., "Protein Production by Auto-Induction in High-Density Shaking Cultures," Protein Expression and Purification 41(1):207-234, May 2005.

Sun, H.-W., et al., "Enlarging the Substrate Binding Pocket of Yeast Alcohol Dehydrogenase I," FASEB Journal (Federation of American Societies for Experimental Biology) 5(5):A1150, Abstract 4518, Mar. 1991.

Tarasow, T.M., et al., "RNA-Catalysed Carbon—Carbon Bond Formation," Nature 389(6646)54-57, Sep. 1997.

Tarasow, T.M., and B.E. Eaton, "The Diels-Alder Reaction and Biopolymer Catalysis," Cellular and Molecular Life Sciences 55(11):1463-1472, Aug. 1999.

Tomatis, P.E., et al., "Mimicking Natural Evolution in Metallo-β-Lactamases Through Second-Shell Ligand Mutations," Proceedings of the National Academy of Sciences of the United States of America (PNAS) 102(39):13761-13766, Sep. 2005.

Venkitasubramanian, P., et al., "Reduction of Carboxylic Acids by Nocardia Aldehyde Oxidoreductase Requires a Phosphopantetheinylated Enzyme," Journal of Biological Chemistry 282(1):478-485, Jan. 2007.

Wentworth, P., Jr., "Antibody Design by Man and Nature," Science 296(5576):2247-2249, Jun. 2002.

Wolfenden, R., "Analog Approaches to the Structure of the Transition State in Enzyme Reactions," Accounts of Chemical Research 5(1):10-18, Jan. 1972.

Wolfenden, R., and M.J. Snider, "The Depth of Chemical Time and the Power of Enzymes as Catalysts," Accounts of Chemical Research 34(12):938-945, Dec. 2001.

Wu, H., et al., "Effects of Modification of Silica Gel and ADH on Enzyme Activity for Enzymatic Conversion of $Co_2$ to Methanol," Catalysis Today 98(4):545-552, Dec. 2004.

Arnold, F.H., "Design by Directed Evolution," Accounts of Chemical Research 31(3):125-131, Mar. 1998.

Ashworth, J., et al., "Computational Redesign of Endonuclease DNA Binding and Cleavage Specificity," Nature 441(7093):656-659, Jun. 2006.

Ballinger, M.D., et al., "Furilisin: A Variant of Subtilisin BPN' Engineered for Cleaving Tribasic Substrates," Biochemistry 35(42):13579-13585, Oct. 1996.

Berson, J.A., "Discoveries Missed, Discoveries Made: Creativity, Influence, and Fame in Chemistry," Tetrahedron 48(1): Jan. 3-17, 1992.

Black, M.E., et al.,"Creation of Drug-Specific Herpes Simplex Virus Type 1 Thymidine Kinase Mutants for Gene Therapy," Proceedings of the National Academy of Sciences of the United States of America (PNAS) 93(8):3525-3529, Apr. 1996.

Bolon, D.N., and S.L. Mayo, "Enzyme-Like Proteins by Computational Design," Proceedings of the National Academy of Sciences of the United States of America (PNAS) 98(25):14274-14279, Dec. 2001.

Bostian, K.A., and G.F. Betts, "Kinetics and Reaction Mechanism of Potassium-Activated Aldehyde Dehydrogenase From *Saccharomyces cerevisiae*," Biochemical Journal 173(3):787-798, Sep. 1978.

Braha, O., et al., "Designed Protein Pores as Components for Biosensors," Chemistry & Biology 4(7):497-505, Jul. 1997.

Braisted, A.C., and P.G. Schultz, "An Antibody-Catalyzed Bimolecular Diels—Alder Reaction," Journal of the American Chemical Society 112(20):7430-7431, Sep. 1990.

Braiuca, P., et al., "Computational Methods to Rationalize Experimental Strategies in Biocatalysis," Trends in Biotechnology 24(9):419-425, Sep. 2006.

(56) References Cited

OTHER PUBLICATIONS

Brandt, G.S., et al., "Probing the Active Center of Benzaldehyde Lyase With Substitutions and the Pseudo-Substrate Analog Benzoylphosphonic Acid Methyl Ester," Biochemistry 47(29):7734-7743, Jul. 2008.

Breslow, R., "On the Mechanism of the Formose Reaction," Tetrahedron Letters 1(21):1-26, 1959.

Breslow, R., et al., "Methylated Cyclodextrin and a Cyclodextrin Polymer as Catalysts in Selective Anisole Chlorination" Tetrahedron Letters 17(20):1645-1646, May 1976.

Burton, R.M., and E.R. Stadtman, "The Oxidation of Acetaldehyde to Acetyl Coenzyme A," Journal of Biological Chemistry 202(2):873-890, Jun. 1953.

Chakraborty, S., et al., "Mechanism of Benzaldehyde Lyase Studied Via Thiamin Diphosphate-Bound Intermediates and Kinetic Isotope Effects," Biochemistry 47(12):3800-3809, Mar. 2008.

Chang, A., et al., "Brenda, Amenda and Frenda the Enzyme Information System: New Content and Tools in 2009," Nucleic Acids Research 37(Database issue):D588-D592, Jan. 2009.

Chang, T.K., et al., "Subtiligase: A Tool for Semisynthesis of Proteins," Proceedings of the National Academy of Sciences of the United States of America (PNAS) 91(26):12544-12548, Dec. 1994.

Chen, R., et al., "Redesigning Secondary Structure to Invert Coenzyme Specificity in Isopropylmalate Dehydrogenase," Proceedings of the National Academy of Sciences of the United States of America (PNAS) 93(22):12171-12176, Oct. 1996.

Chica, R.A. et al., "Semi-Rational Approaches to Engineering Enzyme Activity: Combining the Benefits of Directed Evolution and Rational Design," Current Opinion in Biotechnology 16(4)378-384, Aug. 2005.

Coleman, J.E., and P. Gettins, "Alkaline Phosphatase, Solution Structure, and Mechanism," in A. Meister (ed.), "Advances in Enzymology and Related Areas of Molecular Biology," John Wiley & Sons, New York, 1983, vol. 55, pp. 381-452.

Crameri, A., et al., "Molecular Evolution of an Arsenate Detoxification Pathway by DNA Shuffling," Nature Biotechnology 15(5):436-438, May 1997.

Dunbrack, R.L., Jr., and F.E. Cohen, "Bayesian Statistical Analysis of Protein Side-Chain Rotamer Preferences," Protein Science 6(8):1661-1681, Aug. 1997.

Fortman, J.L., et al., "Biofuel Alternatives to Ethanol: Pumping the Microbial Well," Trends in Biotechnology 26(7):375-381, Jul. 2008.

Foster, W.E., "The Supposed Presence of Formaldehyde-Polymerizing Enzymes in Green Leaves," New Phytologist 44(1): Jun. 17-24, 1945.

Fujii, Y., et al., "The Artificial Evolution of an Enzyme by Random Mutagenesis: The Development of Formaldehyde Dehydrogenase," Bioscience, Biotechnology, and Biochemistry 68(8):1722-1727, Aug. 2004.

García, J.I., et al., "The Source of the endo Rule in the Diels—Alder Reaction: Are Secondary Orbital Interactions Really Necessary?" European Journal of Organic Chemistry 2005(1):85-90, Jan. 2005.

González, B., and R. Vicuña,"Benzaldehyde Lyase, a Novel Thiamine PPi-Requiring Enzyme, From *Pseudomonas fluorescens* Biovar I," Journal of Bacteriology 171(5):2401-2405, May 1989.

Gouverneur, V.E., et al., "Control of the Exo and Endo Pathways of the Diels-Alder Reaction by Antibody Catalysis," Science 262(5131)204-208, Oct. 1993.

Gräslund, S., et al., "Protein Production and Purification," Nature Methods 5(2):135-146, Feb. 2008.

Green, D.W., et al., "Inversion of the Substrate Specificity of Yeast Alcohol Dehydrogenase," Journal of Biological Chemistry 268(11):7792-7798, Apr. 1993.

Hancock, S.M., et al., "Engineering of Glycosidases and Glycosyltransferases," Current Opinion in Chemical Biology 10(5):509-519, Oct. 2006.

Harris, J.L., and C.S. Craik, "Engineering Enzyme Specificity," Current Opinion in Chemical Biology 2(1):127-132, Feb. 1998.

Hawkins, C.F., et al., "A Common Structural Motif in Thiamin Pyrophosphate-Binding Enzymes," FEBS Letters 255(1):77-82, Sep. 1989.

Hendershot, R.J., et al., "High-Throughput Heterogeneous Catalytic Science," Chemistry 11(3):806-814, Jan. 2005.

Hilvert, D., et al., "Antibody Catalysis of the Diels—Alder Reaction," Journal of the American Chemical Society 111(26):9261-9262, Dec. 1989.

Hoover, D.M., and J. Lubkowski, "DNAWorks: An Automated Method for Designing Oligonucleotides for PCR-Based Gene Synthesis," Nucleic Acids Research 30(10):e43, May 2002, 7 pages.

International Search Report and Written Opinion mailed Apr. 9, 2012, issued in corresponding International Appl. No. PCT/US2011/051847, filed Sep. 15, 2011, 9 pages.

Ishige, T., et al., "Long-Chain Aldehyde Dehydrogenase That Participates in n-Alkane Utilization and Wax Ester Synthesis in Acinetobacter sp. Strain M-1," Applied and Environmental Microbiology 66(8):3481-3486, Aug. 2000.

Ito, K., et al., "Cloning and High-Level Expression of the Glutathione-Independent Formaldehyde Dehydrogenase Gene From *Pseudomonas putida*," Journal of Bacteriology 176(9):2483-2491, May 1994.

Jackson, D.Y., et al., "A Designed Peptide Ligase for Total Synthesis of Ribonuclease A With Unnatural Catalytic Residues," Science 266(5183):243-247, Oct. 1994.

Janson, C.A., and W.W. Cleland, "The Kinetic Mechanism of Glycerokinase," Journal of Biological Chemistry 249(8):2562-2566, Apr. 1974.

Janzen, E., et al., "Characterization of Benzaldehyde Lyase From *Pseudomonas fluorescens*: A Versatile Enzyme for Asymmetric C—C Bond Formation," Bioorganic Chemistry 34(6)345-361, Dec. 2006.

Jiang, L., et al., "De Novo Computational Design of Retro-Aldol Enzymes," Science 319(5868):1387-1391, Mar. 2008.

Kang, J., et al., "Self-Assembled Molecular Capsule Catalyzes a Diels—Alder Reaction," Journal of the American Chemical Society 120(29):7389-7390, Jul. 1998.

Karsten, W.E., et al., "Kinetic Studies of L-Aspartase From *Escherichia coli*: Substrate Activation," Biochemistry 25(6):1299-1303, Mar. 1986.

Kim, S.P., et al., "The Origins of Noncovalent Catalysis of Intermolecular Diels—Alder Reactions by Cyclodextrins, Self-Assembling Capsules, Antibodies, and RNAses," Journal of Organic Chemistry 67(12):4250-4260, Jun. 2002.

Korkegian, A., et al., "Computational Thermostabilization of an Enzyme," Science 308(5723):857-860, May 2005.

Kortemme, T., and D. Baker, "A Simple Physical Model for Binding Energy Hot Spots in Protein—Protein Complexes," Proceedings of the National Academy of Sciences of the United States of America (PNAS) 99(22):14116-14121, Oct. 2002.

Kuchner, O., and. F.H. Arnold, "Directed Evolution of Enzyme Catalysts," Trends in Biotechnology 15(12):523-530, Dec. 1997.

Kuhlman, B., and D. Baker, "Exploring Folding Free Energy Landscapes Using Computational Protein Design," Current Opinion in Structural Biology 14(1):89-95, Feb. 2004.

Peeters, D., and G. Leroy, "A Theoretical Approach to the Acid-Catalyzed Hydration of the Carbonyl Group: The Case of Formaldehyde," Canadian Journal of Chemistry 69(9)1376-1387, Sep. 1991.

Pinto, A.L., et al., "Construction of a Catalytically Active Iron Superoxide Dismutase by Rational Protein Design," Proceedings of the National Academy of Sciences of the United States of America (PNAS) 94(11):5562-5567, May 1997.

Pohl, M., et al., "A New Perspective on Thiamine Catalysis," Current Opinion in Biotechnology 15(4):335-342, Aug. 2004.

Powell, K.A., et al., "Directed Evolution and Biocatalysis," Angewandte Chemie: International Edition 40(21):3948-3959, Nov. 2001.

Ramachandran, G.N., et al., "Stereochemistry of Polypeptide Chain Configurations," Journal of Molecular Biology 7:95-99, Jul. 1963.

Rideout, D.C., and R. Breslow, "Hydrophobic Acceleration of Diels—Alder Reactions," Journal of the American Chemical Society 102(26):7816-7817, Dec. 1980.

(56) References Cited

OTHER PUBLICATIONS

Ro, D.K., et al., "Production of the Antimalarial Drug Precursor Artemisinic Acid in Engineered Yeast," Nature 440(7086):940-943, Apr. 2006.

Rohl, C.A., et al., "Protein Structure Prediction Using Rosetta," Methods in Enzymology: Numerical Computer Methods 383:66-93, 2004.

Rothlisberger, D., et al., "Kemp Elimination Catalysts by Computational Enzyme Design," Nature 453(7192):190-195, May 2008.

Rothman, S.C., and J.F. Kirsch, "How Does an Enzyme Evolved In Vitro Compare to Naturally Occurring Homologs Possessing the Targeted Function? Tyrosine Aminotransferase From Aspartate Aminotransferase," Journal of Molecular Biology 327(3):593-608, Mar. 2003.

Schenk, G., et al., "Molecular Evolutionary Analysis of the Thiamine-Diphosphate-Dependent Enzyme, Transketolase," Journal of Molecular Evolution 44(5):552-572, May 1997.

* cited by examiner

SEQUENCE LISTING

```
<160> NUMBER OF SEQ ID NOS: 11

<210> SEQ ID NO 1
<211> LENGTH: 1725
<212> TYPE: DNA
<213> ORGANISM: Artificial sequence
<220> FEATURE:
<223> OTHER INFORMATION: Synthetic
<220> FEATURE:
<221> NAME/KEY: CDS
<222> LOCATION: (1)..(1725)

<400> SEQUENCE: 1 atg gct atg att act ggt ggt gaa ctg gtt gtt cgt acc ctg att aaa      48
Met Ala Met Ile Thr Gly Gly Glu Leu Val Val Arg Thr Leu Ile Lys
1               5                   10                  15 gct ggc gta gaa cat ctg ttt ggc ctg cat ggc gcg cat att gac acc      96
Ala Gly Val Glu His Leu Phe Gly Leu His Gly Ala His Ile Asp Thr
            20                  25                  30 att ttt cag gct tgc ctg gac cac gac gtc cca atc att gat act cgc     144
Ile Phe Gln Ala Cys Leu Asp His Asp Val Pro Ile Ile Asp Thr Arg
        35                  40                  45 cac gaa gcg gcg gca ggc cac gct gcg gaa ggt tat gcc cgc gcg ggc     192
His Glu Ala Ala Ala Gly His Ala Ala Glu Gly Tyr Ala Arg Ala Gly
    50                  55                  60 gct aaa ctg ggt gtt gcc ctg gtg acc gct ggc ggt ggc ttt acc aat     240
Ala Lys Leu Gly Val Ala Leu Val Thr Ala Gly Gly Gly Phe Thr Asn
```

```
            65                  70                  75                  80
gcc gtt acg ccg atc gcg aac gct tgg ctg gat cgc act ccg gtt ctg          288
Ala Val Thr Pro Ile Ala Asn Ala Trp Leu Asp Arg Thr Pro Val Leu
                        85                  90                  95 ttc ctg acc ggt tct ggt gca ctt cgt gat gac gaa acc aac acc ctg          336
Phe Leu Thr Gly Ser Gly Ala Leu Arg Asp Asp Glu Thr Asn Thr Leu
                100                 105                 110 cag gcc ggt att gat cag gtg gcc atg gcg gcc ccg atc acg aaa tgg          384
Gln Ala Gly Ile Asp Gln Val Ala Met Ala Ala Pro Ile Thr Lys Trp
            115                 120                 125 gct cat cgt gtt atg gca act gaa cac atc ccg cgt ctg gtt atg cag          432
Ala His Arg Val Met Ala Thr Glu His Ile Pro Arg Leu Val Met Gln
        130                 135                 140 gcc att cgt gcc gct ctg agc gcc cca cgt ggc ccg gtg ctg ctg gat          480
Ala Ile Arg Ala Ala Leu Ser Ala Pro Arg Gly Pro Val Leu Leu Asp
145                 150                 155                 160 ctg cca tgg gac atc ctg atg aac caa atc gat gaa gat tcc gtt atc          528
Leu Pro Trp Asp Ile Leu Met Asn Gln Ile Asp Glu Asp Ser Val Ile
                165                 170                 175 atc cca gac ctg gtg ctg tct gct cac ggt gcc cgc cca gac ccg gct          576
Ile Pro Asp Leu Val Leu Ser Ala His Gly Ala Arg Pro Asp Pro Ala
            180                 185                 190 gac ctg gac cag gct ctg gca ctg ctg cgt aaa gcc gaa cgc cca gtt          624
Asp Leu Asp Gln Ala Leu Ala Leu Leu Arg Lys Ala Glu Arg Pro Val
        195                 200                 205 atc gta ctg ggc tcc gag gcg tcc cgc acc gca cgc aag acc gca ctg          672
Ile Val Leu Gly Ser Glu Ala Ser Arg Thr Ala Arg Lys Thr Ala Leu
    210                 215                 220 agc gca ttc gta gcg gcg acc ggt gta ccg gtt ttc gct gac tat gaa          720
Ser Ala Phe Val Ala Ala Thr Gly Val Pro Val Phe Ala Asp Tyr Glu
225                 230                 235                 240 ggc ctg tcc atg ctg agc ggc ctg ccg gac gct atg cgt ggc ggc ctg          768
Gly Leu Ser Met Leu Ser Gly Leu Pro Asp Ala Met Arg Gly Gly Leu
                245                 250                 255 gtg cag aac ctg tac tcc ttt gca aaa gct gat gca gct ccg gac ctg          816
Val Gln Asn Leu Tyr Ser Phe Ala Lys Ala Asp Ala Ala Pro Asp Leu
            260                 265                 270 gta ctg atg ctg ggt gct cgt ttc ggt ctg aac acc ggt cat ggt tcc          864
Val Leu Met Leu Gly Ala Arg Phe Gly Leu Asn Thr Gly His Gly Ser
        275                 280                 285 ggt caa ctg atc ccg cat tct gct cag gtg atc cag gtg gat cca gac          912
Gly Gln Leu Ile Pro His Ser Ala Gln Val Ile Gln Val Asp Pro Asp
    290                 295                 300 gcg tgt gaa ctg ggt cgc ctg caa ggc atc gcg ctg ggt atc gtg gct          960
Ala Cys Glu Leu Gly Arg Leu Gln Gly Ile Ala Leu Gly Ile Val Ala
305                 310                 315                 320 gat gta ggt ggc acc att gaa gcg ctg gct cag gcg acc gca cag gac          1008
Asp Val Gly Gly Thr Ile Glu Ala Leu Ala Gln Ala Thr Ala Gln Asp
                325                 330                 335 gcc gcg tgg ccg gac cgc ggc gac tgg tgc gcc aag gta act gac ctg          1056
Ala Ala Trp Pro Asp Arg Gly Asp Trp Cys Ala Lys Val Thr Asp Leu
            340                 345                 350 gcc cag gag cgt tac gct tcc atc gcg gct aaa tcc agc tct gaa cat          1104
Ala Gln Glu Arg Tyr Ala Ser Ile Ala Ala Lys Ser Ser Ser Glu His
        355                 360                 365 gcg ctg cac ccg ttc cac gct tct cag gtt atc gcg aaa cac gtg gac          1152
Ala Leu His Pro Phe His Ala Ser Gln Val Ile Ala Lys His Val Asp
    370                 375                 380 gca ggc gtg acc gtc gtt gcg gat ggt gca ctg act tat ctg tgg ctg          1200
```

```
                                                                        1248
tcc gaa gtt atg tct cgt gtc aaa cca ggc ggc ttc ctg tgc cac ggc
Ser Glu Val Met Ser Arg Val Lys Pro Gly Gly Phe Leu Cys His Gly
405                 410                 415

1296
tat ctg ggc agc atg ggt gta ggc ttc ggt act gcc ctg ggt gcg cag
Tyr Leu Gly Ser Met Gly Val Gly Phe Gly Thr Ala Leu Gly Ala Gln
        420                 425                 430

1344
gtt gcg gat ctg gag gca ggt cgt cgt acc atc ctg gtg acc ggc gac
Val Ala Asp Leu Glu Ala Gly Arg Arg Thr Ile Leu Val Thr Gly Asp
            435                 440                 445

1392
ggc tct gtt ggt tat tcc att ggc gaa ttc gac acc ctg gta cgc aaa
Gly Ser Val Gly Tyr Ser Ile Gly Glu Phe Asp Thr Leu Val Arg Lys
                450                 455                 460

1440
cag ctg ccg ctg att gta att atc atg aac aac cag tct tgg ggc gcg
Gln Leu Pro Leu Ile Val Ile Ile Met Asn Asn Gln Ser Trp Gly Ala
465                 470                 475                 480

1488
acc ctg cac ttt cag cag ctg gcc gtt ggt cct aac cgt gtc acc ggc
Thr Leu His Phe Gln Gln Leu Ala Val Gly Pro Asn Arg Val Thr Gly
        485                 490                 495

1536
acc cgc ctg gaa aat ggt tcc tat cac ggc gtt gct gcg gca ttc ggt
Thr Arg Leu Glu Asn Gly Ser Tyr His Gly Val Ala Ala Ala Phe Gly
            500                 505                 510

1584
gct gat ggt tac cac gtc gac tct gtc gag agc ttc agc gcc gct ctg
Ala Asp Gly Tyr His Val Asp Ser Val Glu Ser Phe Ser Ala Ala Leu
                515                 520                 525

1632
gct cag gca ctg gca cac aac cgc ccg gca tgc atc aac gtt gct gtg
Ala Gln Ala Leu Ala His Asn Arg Pro Ala Cys Ile Asn Val Ala Val
530                 535                 540

1680
gcc ctg gac ccg atc ccg ccg gag gaa ctg atc ctg att ggc atg gac
Ala Leu Asp Pro Ile Pro Pro Glu Glu Leu Ile Leu Ile Gly Met Asp
545                 550                 555                 560

1725
ccg ttt gcg ggc tcc acg gag aat ctg tat ttc caa tcc ggc gcg
Pro Phe Ala Gly Ser Thr Glu Asn Leu Tyr Phe Gln Ser Gly Ala
        565                 570                 575

<210> SEQ ID NO 2
<211> LENGTH: 575
<212> TYPE: PRT
<213> ORGANISM: Artificial sequence
<220> FEATURE:
<223> OTHER INFORMATION: Synthetic Construct

<400> SEQUENCE: 2

Met Ala Met Ile Thr Gly Gly Glu Leu Val Val Arg Thr Leu Ile Lys
1               5                   10                  15

Ala Gly Val Glu His Leu Phe Gly Leu His Gly Ala His Ile Asp Thr
            20                  25                  30

Ile Phe Gln Ala Cys Leu Asp His Asp Val Pro Ile Ile Asp Thr Arg
        35                  40                  45

His Glu Ala Ala Ala Gly His Ala Ala Glu Gly Tyr Ala Arg Ala Gly
    50                  55                  60

Ala Lys Leu Gly Val Ala Leu Val Thr Ala Gly Gly Phe Thr Asn
65                  70                  75                  80

Ala Val Thr Pro Ile Ala Asn Ala Trp Leu Asp Arg Thr Pro Val Leu
            85                  90                  95

Phe Leu Thr Gly Ser Gly Ala Leu Arg Asp Asp Glu Thr Asn Thr Leu
        100                 105                 110

Gln Ala Gly Ile Asp Gln Val Ala Met Ala Ala Pro Ile Thr Lys Trp
```

-continued

```
            115                 120                 125
Ala His Arg Val Met Ala Thr Glu His Ile Pro Arg Leu Val Met Gln
        130                 135                 140
Ala Ile Arg Ala Ala Leu Ser Ala Pro Arg Gly Pro Val Leu Leu Asp
145                 150                 155                 160
Leu Pro Trp Asp Ile Leu Met Asn Gln Ile Asp Glu Asp Ser Val Ile
                165                 170                 175
Ile Pro Asp Leu Val Leu Ser Ala His Gly Ala Arg Pro Asp Pro Ala
                180                 185                 190
Asp Leu Asp Gln Ala Leu Ala Leu Leu Arg Lys Ala Glu Arg Pro Val
                195                 200                 205
Ile Val Leu Gly Ser Glu Ala Ser Arg Thr Ala Arg Lys Thr Ala Leu
        210                 215                 220
Ser Ala Phe Val Ala Ala Thr Gly Val Pro Val Phe Ala Asp Tyr Glu
225                 230                 235                 240
Gly Leu Ser Met Leu Ser Gly Leu Pro Asp Ala Met Arg Gly Gly Leu
                245                 250                 255
Val Gln Asn Leu Tyr Ser Phe Ala Lys Ala Asp Ala Ala Pro Asp Leu
                260                 265                 270
Val Leu Met Leu Gly Ala Arg Phe Gly Leu Asn Thr Gly His Gly Ser
            275                 280                 285
Gly Gln Leu Ile Pro His Ser Ala Gln Val Ile Gln Val Asp Pro Asp
        290                 295                 300
Ala Cys Glu Leu Gly Arg Leu Gln Gly Ile Ala Leu Gly Ile Val Ala
305                 310                 315                 320
Asp Val Gly Gly Thr Ile Glu Ala Leu Ala Gln Ala Thr Ala Gln Asp
                325                 330                 335
Ala Ala Trp Pro Asp Arg Gly Asp Trp Cys Ala Lys Val Thr Asp Leu
                340                 345                 350
Ala Gln Glu Arg Tyr Ala Ser Ile Ala Ala Lys Ser Ser Glu His
                355                 360                 365
Ala Leu His Pro Phe His Ala Ser Gln Val Ile Ala Lys His Val Asp
        370                 375                 380
Ala Gly Val Thr Val Val Ala Asp Gly Ala Leu Thr Tyr Leu Trp Leu
385                 390                 395                 400
Ser Glu Val Met Ser Arg Val Lys Pro Gly Gly Phe Leu Cys His Gly
                405                 410                 415
Tyr Leu Gly Ser Met Gly Val Gly Phe Gly Thr Ala Leu Gly Ala Gln
                420                 425                 430
Val Ala Asp Leu Glu Ala Gly Arg Arg Thr Ile Leu Val Thr Gly Asp
                435                 440                 445
Gly Ser Val Gly Tyr Ser Ile Gly Glu Phe Asp Thr Leu Val Arg Lys
        450                 455                 460
Gln Leu Pro Leu Ile Val Ile Met Asn Asn Gln Ser Trp Gly Ala
465                 470                 475                 480
Thr Leu His Phe Gln Gln Leu Ala Val Gly Pro Asn Arg Val Thr Gly
                485                 490                 495
Thr Arg Leu Glu Asn Gly Ser Tyr His Gly Val Ala Ala Ala Phe Gly
                500                 505                 510
Ala Asp Gly Tyr His Val Asp Ser Val Glu Ser Phe Ser Ala Ala Leu
                515                 520                 525
Ala Gln Ala Leu Ala His Asn Arg Pro Ala Cys Ile Asn Val Ala Val
        530                 535                 540
```

-continued

Ala Leu Asp Pro Ile Pro Pro Glu Glu Leu Ile Leu Ile Gly Met Asp
545                 550                 555                 560

Pro Phe Ala Gly Ser Thr Glu Asn Leu Tyr Phe Gln Ser Gly Ala
                565                 570                 575

<210> SEQ ID NO 3
<211> LENGTH: 602
<212> TYPE: PRT
<213> ORGANISM: Rhodopseudomonas palustris

<400> SEQUENCE: 3

Met Ser Ala Ala Thr Ser Ser Ala Gly Asp Trp Leu Glu Gly Gly Glu
1               5                   10                  15

Leu Leu Ala Arg Thr Leu Arg Asp Ala Gly Val Asp Thr Val Phe Ala
                20                  25                  30

Leu His Gly Gly His Leu Glu Ser Phe Tyr Arg Gly Cys Ile Ala Asn
            35                  40                  45

Asp Ile Arg Leu Val Asp Phe Arg His Glu Ser Ala Gly His Ala
        50                  55                  60

Ala Asp Gly Tyr Ala Arg Ala Thr Gly Lys Leu Gly Val Cys Val Ile
65              70                  75                  80

Thr Ala Gly Pro Gly Phe Thr Asn Gly Val Thr Ala Ile Leu Asn Ala
                85                  90                  95

Gln Leu Asp Ser Ile Pro Thr Leu Phe Ile Val Gly Ser Pro Pro Leu
            100                 105                 110

Arg Glu Ala Glu Thr Asn Ala Leu Gln Gly Gly Val Asp Gln Ile Ala
        115                 120                 125

Val Thr Leu Pro Met Val Lys Tyr Ala His Arg Ile Thr Asn Thr Glu
130                 135                 140

Arg Ile Pro Asp Leu Thr Ala Leu Ala Ile Arg Lys Ala Thr Thr Gly
145                 150                 155                 160

Arg Arg Gly Ala Val Leu Leu Asp Val Pro Ile Asp Val Leu His Met
                165                 170                 175

Arg Ala His Lys Asp Asp Val Arg Pro Ala His Gly Leu Asn Ile Asn
            180                 185                 190

Pro Arg Pro Ala Pro His Pro Asp Glu Ile Lys Ala Ala Ile Ala Ile
        195                 200                 205

Leu Lys Ala Ser Glu Arg Pro Val Ile Val Val Gly Gly Glu Ala Arg
210                 215                 220

Tyr Ser Asn Cys Arg Asp Asp Leu Val Ala Leu Ala Glu Ala Thr Gln
225                 230                 235                 240

Ile Pro Val Val Ser Asn Thr Arg Gly Met Gly Val Phe Pro Ser Ser
                245                 250                 255

His Pro Leu Asn Gly Gln Val Val Gly Asn Leu Ala Leu Leu Ser Ala
            260                 265                 270

Arg Arg Pro Asp Ala Ala Leu Leu Leu Gly Thr Arg Phe Gly Phe Arg
        275                 280                 285

Leu Ala Gly Arg Ser Thr Ala Phe Phe Pro Asp Asp Ala Lys Leu Ile
290                 295                 300

Gln Val His Ser Asp Ala Ala Glu Leu Gly Leu Arg His Val Glu
305                 310                 315                 320

Leu Pro Ile Val Ala Asp Val Gly Ala Ala Leu Thr Thr Leu Arg Thr
                325                 330                 335

Ala Ala Ala Ala Glu Thr Trp Pro Gln Arg Pro Ala Trp Ile Glu Ala

```
                    340             345             350
Val Thr Lys Ala Pro Ala Lys Met Leu Asp Met Phe Pro Asn Lys Gln
        355                 360                 365
Gly Pro Lys Gly Ile His Pro Phe Trp Ala Glu Ala Ala Val Arg
    370                 375                 380
Ala Ala Gly Pro Asp Ala Ile Val Leu Asp Gly Gly Glu Ala Ala
385                 390                 395                 400
Ser Trp Ala Ala Phe His Leu Arg Ser Asn Gln Pro Gly His Val Gln
                405                 410                 415
Gly Val Gly Tyr Leu Gly Cys Leu Gly Thr Gly Pro Gly Gln Ser Ile
            420                 425                 430
Gly Ala Gln Leu Val Asp Pro Asp Lys Arg Val Met Gln Ile Thr Gly
        435                 440                 445
Asp Gly Ala Met Gly Phe His Ile Gln Glu Phe Asp Thr Met Ser Arg
    450                 455                 460
His Arg Leu Pro Ile Cys Thr Ile Val Leu Asn Asn Glu Ile Trp Gly
465                 470                 475                 480
Met Ser Ile His Gly Gln Gln Ile Met Tyr Gly Ala Asn Tyr Ser Ala
                485                 490                 495
Ile Ser Glu Leu Arg Gly Thr Asn Tyr Ala Ser Val Ala Ala Ala Phe
            500                 505                 510
Gly Cys His Ala Glu Arg Val Thr Glu Phe Asp Glu Ile Glu Pro Ala
        515                 520                 525
Ile Ala Arg Ala Tyr Ala Ser Gly Gln Pro Ser Cys Ile Glu Ile Met
    530                 535                 540
Ile Asp Pro Asp Val Val His Pro Val Thr Val Ala Ala Leu Gly Thr
545                 550                 555                 560
Ile Ser Asp Glu Lys Arg Glu Ile Met Ile Pro Tyr Tyr Glu Asn Ile
                565                 570                 575
Pro Ile Arg Pro Gln Ala Gly Ser Thr Glu Asn Leu Tyr Phe Gln Ser
            580                 585                 590
Gly Ala Leu Glu His His His His His His
        595                 600

<210> SEQ ID NO 4
<211> LENGTH: 583
<212> TYPE: PRT
<213> ORGANISM: Artificial sequence
<220> FEATURE:
<223> OTHER INFORMATION: Synthetic

<400> SEQUENCE: 4

Met Ala Met Ile Thr Gly Gly Glu Leu Val Val Arg Thr Leu Ile Lys
1               5                   10                  15
Ala Gly Val Glu His Leu Phe Gly Leu His Gly Ser His Ile Asp Thr
                20                  25                  30
Ile Phe Gln Ala Cys Leu Asp His Asp Val Pro Ile Ile Asp Thr Arg
            35                  40                  45
His Glu Ala Ala Gly His Ala Ala Glu Gly Tyr Ala Arg Ala Gly
        50                  55                  60
Ala Lys Leu Gly Val Ala Leu Val Thr Ala Gly Gly Phe Thr Asn
65                  70                  75                  80
Ala Val Thr Pro Ile Ala Asn Ala Trp Leu Asp Arg Thr Pro Val Leu
                85                  90                  95
Phe Leu Thr Gly Ser Gly Ala Leu Arg Asp Asp Glu Thr Asn Thr Leu
```

```
                100             105                 110
Gln Ala Gly Ile Asp Gln Val Ala Met Ala Pro Ile Thr Lys Trp
            115                 120             125
Ala His Arg Val Met Ala Thr Glu His Ile Pro Arg Leu Val Met Gln
130                 135                 140
Ala Ile Arg Ala Ala Leu Ser Ala Pro Arg Gly Pro Val Leu Leu Asp
145                 150                 155                 160
Leu Pro Trp Asp Ile Leu Met Asn Gln Ile Asp Glu Asp Ser Val Ile
                165                 170                 175
Ile Pro Asp Leu Val Leu Ser Ala His Gly Ala Arg Pro Asp Pro Ala
            180                 185                 190
Asp Leu Asp Gln Ala Leu Ala Leu Leu Arg Lys Ala Glu Arg Pro Val
        195                 200                 205
Ile Val Leu Gly Ser Glu Ala Ser Arg Thr Ala Arg Lys Thr Ala Leu
    210                 215                 220
Ser Ala Phe Val Ala Ala Thr Gly Val Pro Val Phe Ala Asp Tyr Glu
225                 230                 235                 240
Gly Leu Ser Met Leu Ser Gly Leu Pro Asp Ala Met Arg Gly Gly Leu
                245                 250                 255
Val Gln Asn Leu Tyr Ser Phe Ala Lys Ala Asp Ala Ala Pro Asp Leu
            260                 265                 270
Val Leu Met Leu Gly Ala Arg Phe Gly Leu Asn Thr Gly His Gly Ser
        275                 280                 285
Gly Gln Leu Ile Pro His Ser Ala Gln Val Ile Gln Val Asp Pro Asp
    290                 295                 300
Ala Cys Glu Leu Gly Arg Leu Gln Gly Ile Ala Leu Gly Ile Val Ala
305                 310                 315                 320
Asp Val Gly Gly Thr Ile Glu Ala Leu Ala Gln Ala Thr Ala Gln Asp
                325                 330                 335
Ala Ala Trp Pro Asp Arg Gly Asp Trp Cys Ala Lys Val Thr Asp Leu
            340                 345                 350
Ala Gln Glu Arg Tyr Ala Ser Ile Ala Ala Lys Ser Ser Glu His
        355                 360                 365
Ala Leu His Pro Phe His Ala Ser Gln Val Ile Ala Lys His Val Asp
    370                 375                 380
Ala Gly Val Thr Val Val Ala Asp Gly Gly Leu Thr Tyr Leu Trp Leu
385                 390                 395                 400
Ser Glu Val Met Ser Arg Val Lys Pro Gly Gly Phe Leu Cys His Gly
                405                 410                 415
Tyr Leu Gly Ser Met Gly Val Gly Phe Gly Thr Ala Leu Gly Ala Gln
            420                 425                 430
Val Ala Asp Leu Glu Ala Gly Arg Arg Thr Ile Leu Val Thr Gly Asp
        435                 440                 445
Gly Ser Val Gly Tyr Ser Ile Gly Glu Phe Asp Thr Leu Val Arg Lys
    450                 455                 460
Gln Leu Pro Leu Ile Val Ile Met Asn Asn Gln Ser Trp Gly Trp
465                 470                 475                 480
Thr Leu His Phe Gln Gln Leu Ala Val Gly Pro Asn Arg Val Thr Gly
                485                 490                 495
Thr Arg Leu Glu Asn Gly Ser Tyr His Gly Val Ala Ala Phe Gly
            500                 505                 510
Ala Asp Gly Tyr His Val Asp Ser Val Glu Ser Phe Ser Ala Ala Leu
        515                 520                 525
```

Ala Gln Ala Leu Ala His Asn Arg Pro Ala Cys Ile Asn Val Ala Val
            530                 535                 540

Ala Leu Asp Pro Ile Pro Pro Glu Glu Leu Ile Leu Ile Gly Met Asp
545                 550                 555                 560

Pro Phe Ala Gly Ser Thr Glu Asn Leu Tyr Phe Gln Ser Gly Ala Leu
                565                 570                 575

Glu His His His His His His
            580

<210> SEQ ID NO 5
<211> LENGTH: 583
<212> TYPE: PRT
<213> ORGANISM: Artificial sequence
<220> FEATURE:
<223> OTHER INFORMATION: Synthetic

<400> SEQUENCE: 5

Met Ala Met Ile Thr Gly Gly Glu Leu Val Val Arg Thr Leu Ile Lys
1               5                   10                  15

Ala Gly Val Glu His Leu Phe Gly Leu His Gly Ala His Ile Asp Thr
            20                  25                  30

Ile Phe Gln Ala Cys Leu Asp His Asp Val Pro Ile Asp Thr Arg
        35                  40                  45

His Glu Ala Ala Gly His Ala Ala Glu Gly Tyr Ala Arg Ala Gly
    50                  55                  60

Ala Lys Leu Gly Val Ala Leu Val Thr Ala Gly Gly Phe Thr Asn
65                  70                  75                  80

Ala Val Thr Pro Ile Ala Asn Ala Trp Leu Asp Arg Thr Pro Val Leu
                85                  90                  95

Phe Leu Thr Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
        115                 120                 125

Ala His Arg Val Met Ala Thr Glu His Ile Pro Arg Leu Val Met Gln
    130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala Arg Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
    290                 295                 300

-continued

```
Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
            325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
            355                 360                 365

Ala Leu His Pro Phe His Ala Ser Gln Val Ile Ala Lys His Val Asp
        370                 375                 380

Ala Gly Val Thr Val Val Ala Asp Gly Gly Leu Thr Tyr Leu Trp Leu
385                 390                 395                 400

Ser Glu Val Met Ser Arg Val Lys Pro Gly Gly Phe Leu Cys His Gly
                405                 410                 415

Tyr Leu Asn Ser Met Gly Val Gly Phe Gly Thr Ala Leu Gly Ala Gln
                420                 425                 430

Val Ala Asp Leu Glu Ala Gly Arg Arg Thr Ile Leu Val Thr Gly Asp
            435                 440                 445

Gly Ser Val Gly Tyr Ser Ile Gly Glu Phe Asp Thr Leu Val Arg Lys
450                 455                 460

Gln Leu Pro Leu Ile Val Ile Met Asn Asn Gln Ser Trp Gly Trp
465                 470                 475                 480

Thr Leu His Phe Gln Gln Leu Ala Val Gly Pro Asn Arg Val Thr Gly
                485                 490                 495

Thr Arg Leu Glu Asn Gly Ser Tyr His Gly Val Ala Ala Phe Gly
            500                 505                 510

Ala Asp Gly Tyr His Val Asp Ser Val Glu Ser Phe Ser Ala Ala Leu
        515                 520                 525

Ala Gln Ala Leu Ala His Asn Arg Pro Ala Cys Ile Asn Val Ala Val
530                 535                 540

Ala Leu Asp Pro Ile Pro Pro Glu Glu Leu Ile Leu Ile Gly Met Asp
545                 550                 555                 560

Pro Phe Ala Gly Ser Thr Glu Asn Leu Tyr Phe Gln Ser Gly Ala Leu
                565                 570                 575

Glu His His His His His His
            580
```

```
<210> SEQ ID NO 6
<211> LENGTH: 583
<212> TYPE: PRT
<213> ORGANISM: Artificial sequence
<220> FEATURE:
<223> OTHER INFORMATION: Synthetic

<400> SEQUENCE: 6
```

```
Met Ala Met Ile Thr Gly Gly Glu Leu Val Val Arg Thr Leu Ile Lys
1               5                   10                  15

Ala Gly Val Glu His Leu Phe Gly Leu His Gly Ser His Ile Asp Thr
            20                  25                  30

Ile Phe Gln Ala Cys Leu Asp His Asp Val Pro Ile Ile Asp Thr Arg
        35                  40                  45

His Glu Ala Ala Gly His Ala Ala Glu Gly Tyr Ala Arg Ala Gly
    50                  55                  60

Ala Lys Leu Gly Val Ala Leu Val Thr Ala Gly Gly Gly Phe Thr Asn
65                  70                  75                  80
```

```
Ala Val Thr Pro Ile Ala Asn Ala Trp Leu Asp Arg Thr Pro Val Leu
                85                  90                  95

Phe Leu Thr Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
        115                 120                 125

Ala His Arg Val Met Ala Thr Glu His Ile Pro Arg Leu Val Met Gln
130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala Arg Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
        210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
        290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
        370                 375                 380

Ala Gly Val Thr Val Val Ala Asp Gly Ala Leu Thr Tyr Leu Trp Leu
385                 390                 395                 400

Ser Glu Val Met Ser Arg Val Lys Pro Gly Gly Phe Leu Cys His Gly
                405                 410                 415

Tyr Leu Asn Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
        435                 440                 445

Gly Ser Val Gly Tyr Ser Ile Gly Glu Phe Asp Thr Leu Val Arg Lys
        450                 455                 460

Gln Leu Pro Leu Ile Val Ile Met Asn Asn Gln Ser Trp Gly Trp
465                 470                 475                 480

Thr Leu His Phe Gln Gln Leu Ala Val Gly Pro Asn Arg Val Thr Gly
                485                 490                 495
```

Thr Arg Leu Glu Asn Gly Ser Tyr His Gly Val Ala Ala Phe Gly
            500                 505                 510

Ala Asp Gly Tyr His Val Asp Ser Val Glu Ser Phe Ser Ala Ala Leu
        515                 520                 525

Ala Gln Ala Leu Ala His Asn Arg Pro Ala Cys Ile Asn Val Ala Val
    530                 535                 540

Ala Leu Asp Pro Ile Pro Glu Glu Leu Ile Leu Ile Gly Met Asp
545                 550                 555                 560

Pro Phe Ala Gly Ser Thr Glu Asn Leu Tyr Phe Gln Ser Gly Ala Leu
                565                 570                 575

Glu His His His His His His
            580

<210> SEQ ID NO 7
<211> LENGTH: 583
<212> TYPE: PRT
<213> ORGANISM: Artificial sequence
<220> FEATURE:
<223> OTHER INFORMATION: Synthetic

<400> SEQUENCE: 7

Met Ala Met Ile Thr Gly Gly Glu Leu Val Val Arg Thr Leu Ile Lys
1               5                   10                  15

Ala Gly Val Glu His Leu Phe Gly Leu His Gly Ser His Ile Asp Thr
            20                  25                  30

Ile Phe Gln Ala Cys Leu Asp His Asp Val Pro Ile Ile Asp Thr Arg
        35                  40                  45

His Glu Ala Ala Ala Gly His Ala Ala Glu Gly Tyr Ala Arg Ala Gly
    50                  55                  60

Ala Lys Leu Gly Val Ala Leu Val Thr Ala Gly Gly Gly Phe Thr Asn
65                  70                  75                  80

Ala Val Thr Pro Ile Ala Asn Ala Trp Leu Asp Arg Thr Pro Val Leu
                85                  90                  95

Phe Leu Thr Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
        115                 120                 125

Ala His Arg Val Met Ala Thr Glu His Ile Pro Arg Leu Val Met Gln
    130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala Arg Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
            275                 280                 285

Gly Gln Leu Ile Pro His Ser Ala Gln Val Ile Gln Val Asp Pro Asp
290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
                340                 345                 350

Ala Gln Glu Arg Tyr Ala Ser Ile Ala Ala Lys Ser Ser Glu His
                355                 360                 365

Ala Leu His Pro Phe His Ala Ser Gln Val Ile Ala Lys His Val Asp
                370                 375                 380

Ala Gly Val Thr Val Val Ala Asp Gly Gly Leu Thr Tyr Leu Trp Leu
385                 390                 395                 400

Ser Glu Val Met Ser Arg Val Lys Pro Gly Gly Phe Leu Cys His Gly
                405                 410                 415

Tyr Leu Asn Ser Met Gly Val Gly Phe Gly Thr Ala Leu Gly Ala Gln
                420                 425                 430

Val Ala Asp Leu Glu Ala Gly Arg Arg Thr Ile Leu Val Thr Gly Asp
                435                 440                 445

Gly Ser Val Gly Tyr Ser Ile Gly Glu Phe Asp Thr Leu Val Arg Lys
                450                 455                 460

Gln Leu Pro Leu Ile Val Ile Met Asn Asn Gln Ser Trp Gly Ala
465                 470                 475                 480

Thr Leu His Phe Gln Gln Leu Ala Val Gly Pro Asn Arg Val Thr Gly
                485                 490                 495

Thr Arg Leu Glu Asn Gly Ser Tyr His Gly Val Ala Ala Phe Gly
                500                 505                 510

Ala Asp Gly Tyr His Val Asp Ser Val Glu Ser Phe Ser Ala Ala Leu
                515                 520                 525

Ala Gln Ala Leu Ala His Asn Arg Pro Ala Cys Ile Asn Val Ala Val
530                 535                 540

Ala Leu Asp Pro Ile Pro Pro Glu Glu Leu Ile Leu Ile Gly Met Asp
545                 550                 555                 560

Pro Phe Ala Gly Ser Thr Glu Asn Leu Tyr Phe Gln Ser Gly Ala Leu
                565                 570                 575

Glu His His His His His His
            580

<210> SEQ ID NO 8
<211> LENGTH: 583
<212> TYPE: PRT
<213> ORGANISM: Artificial sequence
<220> FEATURE:
<223> OTHER INFORMATION: Synthetic

<400> SEQUENCE: 8

Met Ala Met Ile Thr Gly Gly Glu Leu Val Val Arg Thr Leu Ile Lys
1               5                   10                  15

Ala Gly Val Glu His Leu Phe Gly Leu His Gly Ser His Ile Asp Thr
                20                  25                  30

Ile Phe Gln Ala Cys Leu Asp His Asp Val Pro Ile Ile Asp Thr Arg
            35                  40                  45

-continued

```
His Glu Ala Ala Ala Gly His Ala Ala Glu Gly Tyr Ala Arg Ala Gly
 50                  55                  60

Ala Lys Leu Gly Val Ala Leu Val Thr Ala Gly Gly Phe Thr Asn
 65                  70                  75                  80

Ala Val Thr Pro Ile Ala Asn Ala Trp Leu Asp Arg Thr Pro Val Leu
                 85                  90                  95

Phe Leu Thr Gly Ser Gly Ala Leu Arg Asp Asp Glu Thr Asn Thr Leu
                100                 105                 110

Gln Ala Gly Ile Asp Gln Val Ala Met Ala Ala Pro Ile Thr Lys Trp
            115                 120                 125

Ala His Arg Val Met Ala Thr Glu His Ile Pro Arg Leu Val Met Gln
130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala Arg Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
                245                 250                 255

Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
    290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
    370                 375                 380

Ala Gly Val Thr Val Ala Asp Gly Gly Leu Thr Tyr Leu Trp Leu
385                 390                 395                 400

Ser Glu Val Met Ser Arg Val Lys Pro Gly Gly Phe Leu Cys His Gly
                405                 410                 415

Tyr Leu Asn Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
        435                 440                 445

Gly Ser Val Gly Tyr Ser Ile Gly Glu Phe Asp Thr Leu Val Arg Lys
    450                 455                 460

Gln Leu Pro Leu Ile Val Ile Ile Met Asn Asn Gln Ser Trp Gly Trp
```

```
                465                 470                 475                 480
Thr Leu His Phe Gln Gln Leu Ala Val Gly Pro Asn Arg Val Thr Gly
                    485                 490                 495

Thr Arg Leu Glu Asn Gly Ser Tyr His Gly Val Ala Ala Phe Gly
            500                 505                 510

Ala Asp Gly Tyr His Val Asp Ser Val Glu Ser Phe Ser Ala Ala Leu
            515                 520                 525

Ala Gln Ala Leu Ala His Asn Arg Pro Ala Cys Ile Asn Val Ala Val
        530                 535                 540

Ala Leu Asp Pro Ile Pro Pro Glu Glu Leu Ile Leu Ile Gly Met Asp
545                 550                 555                 560

Pro Phe Ala Gly Ser Thr Glu Asn Leu Tyr Phe Gln Ser Gly Ala Leu
                565                 570                 575

Glu His His His His His His
            580

<210> SEQ ID NO 9
<211> LENGTH: 583
<212> TYPE: PRT
<213> ORGANISM: Artificial sequence
<220> FEATURE:
<223> OTHER INFORMATION: Synthetic

<400> SEQUENCE: 9

Met Ala Met Ile Thr Gly Gly Glu Leu Val Arg Thr Leu Ile Lys
1               5                   10                  15

Ala Gly Val Glu His Leu Phe Gly Leu His Gly Ile His Ile Asp Thr
            20                  25                  30

Ile Phe Gln Ala Cys Leu Asp His Asp Val Pro Ile Ile Asp Thr Arg
        35                  40                  45

His Glu Ala Ala Ala Gly His Ala Ala Glu Gly Tyr Ala Arg Ala Gly
    50                  55                  60

Ala Lys Leu Gly Val Ala Leu Val Thr Ala Gly Gly Phe Thr Asn
65                  70                  75                  80

Ala Val Thr Pro Ile Ala Asn Ala Trp Leu Asp Arg Thr Pro Val Leu
                85                  90                  95

Phe Leu Thr Gly Ser Gly Ala Leu Arg Asp Asp Glu Thr Asn Thr Leu
            100                 105                 110

Gln Ala Gly Ile Asp Gln Val Ala Met Ala Ala Pro Ile Thr Lys Trp
        115                 120                 125

Ala His Arg Val Met Ala Thr Glu His Ile Pro Arg Leu Val Met Gln
    130                 135                 140

Ala Ile Arg Ala Ala Leu Ser Ala Pro Arg Gly Pro Val Leu Leu Asp
145                 150                 155                 160

Leu Pro Trp Asp Ile Leu Met Asn Gln Ile Asp Glu Asp Ser Val Ile
                165                 170                 175

Ile Pro Asp Leu Val Leu Ser Ala His Gly Ala Arg Pro Asp Pro Ala
            180                 185                 190

Asp Leu Asp Gln Ala Leu Ala Leu Leu Arg Lys Ala Glu Arg Pro Val
        195                 200                 205

Ile Val Leu Gly Ser Glu Ala Ser Arg Thr Ala Arg Lys Thr Ala Leu
    210                 215                 220

Ser Ala Phe Val Ala Ala Thr Gly Val Pro Val Phe Ala Asp Tyr Glu
225                 230                 235                 240

Gly Leu Ser Met Leu Ser Gly Leu Pro Asp Ala Met Arg Gly Gly Leu
```

```
                245                 250                 255
Val Gln Asn Leu Tyr Ser Phe Ala Lys Ala Asp Ala Ala Pro Asp Leu
            260                 265                 270

Val Leu Met Leu Gly Ala Arg Phe Gly Leu Asn Thr Gly His Gly Ser
        275                 280                 285

Gly Gln Leu Ile Pro His Ser Ala Gln Val Ile Gln Val Asp Pro Asp
    290                 295                 300

Ala Cys Glu Leu Gly Arg Leu Gln Gly Ile Ala Leu Gly Ile Val Ala
305                 310                 315                 320

Asp Val Gly Gly Thr Ile Glu Ala Leu Ala Gln Ala Thr Ala Gln Asp
                325                 330                 335

Ala Ala Trp Pro Asp Arg Gly Asp Trp Cys Ala Lys Val Thr Asp Leu
            340                 345                 350

Ala Gln Glu Arg Tyr Ala Ser Ile Ala Ala Lys Ser Ser Glu His
        355                 360                 365

Ala Leu His Pro Phe His Ala Ser Gln Val Ile Ala Lys His Val Asp
    370                 375                 380

Ala Gly Val Thr Val Ala Asp Gly Gly Leu Thr Tyr Leu Trp Leu
385                 390                 395                 400

Ser Glu Val Met Ser Arg Val Lys Pro Gly Phe Leu Cys His Gly
                405                 410                 415

Tyr Leu Asn Ser Met Gly Val Gly Phe Gly Thr Ala Leu Gly Ala Gln
            420                 425                 430

Val Ala Asp Leu Glu Ala Gly Arg Arg Thr Ile Leu Val Thr Gly Asp
        435                 440                 445

Gly Ser Val Gly Tyr Ser Ile Gly Glu Phe Asp Thr Leu Val Arg Lys
    450                 455                 460

Gln Leu Pro Leu Ile Val Ile Met Asn Asn Gln Ser Trp Gly Trp
465                 470                 475                 480

Thr Leu His Phe Gln Gln Leu Ala Val Gly Pro Asn Arg Val Thr Gly
                485                 490                 495

Thr Arg Leu Glu Asn Gly Ser Tyr His Gly Val Ala Ala Phe Gly
            500                 505                 510

Ala Asp Gly Tyr His Val Asp Ser Val Glu Ser Phe Ser Ala Ala Leu
        515                 520                 525

Ala Gln Ala Leu Ala His Asn Arg Pro Ala Cys Ile Asn Val Ala Val
    530                 535                 540

Ala Leu Asp Pro Ile Pro Pro Glu Glu Leu Ile Leu Ile Gly Met Asp
545                 550                 555                 560

Pro Phe Ala Gly Ser Thr Glu Asn Leu Tyr Phe Gln Ser Gly Ala Leu
                565                 570                 575

Glu His His His His His
            580

<210> SEQ ID NO 10
<211> LENGTH: 674
<212> TYPE: PRT
<213> ORGANISM: Escherichia coli

<400> SEQUENCE: 10

Met Ser Gln Ile His Lys His Thr Ile Pro Ala Asn Ile Ala Asp Arg
1               5                   10                  15

Cys Leu Ile Asn Pro Gln Gln Tyr Glu Ala Met Tyr Gln Gln Ser Ile
            20                  25                  30
```

```
Asn Val Pro Asp Thr Phe Trp Gly Glu Gln Gly Lys Ile Leu Asp Trp
         35                  40                  45

Ile Lys Pro Tyr Gln Lys Val Lys Asn Thr Ser Phe Ala Pro Gly Asn
 50                  55                  60

Val Ser Ile Lys Trp Tyr Glu Asp Gly Thr Leu Asn Leu Ala Ala Asn
 65                  70                  75                  80

Cys Leu Asp Arg His Leu Gln Glu Asn Gly Asp Arg Thr Ala Ile Ile
                 85                  90                  95

Trp Glu Gly Asp Asp Ala Ser Gln Ser Lys His Ile Ser Tyr Lys Glu
                100                 105                 110

Leu His Arg Asp Val Cys Arg Phe Ala Asn Thr Leu Leu Glu Leu Gly
             115                 120                 125

Ile Lys Lys Gly Asp Val Val Ala Ile Tyr Met Pro Met Val Pro Glu
 130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Asn Ser Arg Leu Val Ile Thr Ser Asp Glu Gly Val Arg Ala
             180                 185                 190

Gly Arg Ser Ile Pro Leu Lys Lys Asn Val Asp Asp Ala Leu Lys Asn
         195                 200                 205

Pro Asn Val Thr Ser Val Glu His Val Val Leu Lys Arg Thr Gly
 210                 215                 220

Gly Lys Ile Asp Trp Gln Glu Gly Arg Asp Leu Trp Trp His Asp Leu
225                 230                 235                 240

Val Glu Gln Ala Ser Asp Gln His Gln Ala Glu Glu Met Asn Ala Glu
                245                 250                 255

Asp Pro Leu Phe Ile Leu Tyr Thr Ser Gly Ser Thr Gly Lys Pro Lys
             260                 265                 270

Gly Val Leu His Thr Thr Gly Gly Tyr Leu Val Tyr Ala Ala Leu Thr
         275                 280                 285

Phe Lys Tyr Val Phe Asp Tyr His Pro Gly Asp Ile Tyr Trp Cys Thr
 290                 295                 300

Ala Asp Val Gly Trp Val Thr Gly His Ser Tyr Leu Leu Tyr Gly Pro
305                 310                 315                 320

Leu Ala Cys Gly Ala Thr Thr Leu Met Phe Glu Gly Val Pro Asn Trp
                325                 330                 335

Pro Thr Pro Ala Arg Met Ala Gln Val Val Asp Lys His Gln Val Asn
             340                 345                 350

Ile Leu Tyr Thr Ala Pro Thr Ala Ile Arg Ala Leu Met Ala Glu Gly
         355                 360                 365

Asp Lys Ala Ile Glu Gly Thr Asp Arg Ser Ser Leu Arg Ile Leu Gly
 370                 375                 380

Ser Val Gly Glu Pro Ile Asn Pro Glu Ala Trp Glu Trp Tyr Trp Lys
385                 390                 395                 400

Lys Ile Gly Asn Glu Lys Cys Pro Val Val Asp Thr Trp Trp Gln Thr
                405                 410                 415

Glu Thr Gly Gly Phe Met Ile Thr Pro Leu Pro Gly Ala Thr Glu Leu
             420                 425                 430

Lys Ala Gly Ser Ala Thr Arg Pro Phe Phe Gly Val Gln Pro Ala Leu
         435                 440                 445

Val Asp Asn Glu Gly Asn Pro Leu Glu Gly Ala Thr Glu Gly Ser Leu
```

```
                450           455           460
Val Ile Thr Asp Ser Trp Pro Gly Gln Ala Arg Thr Leu Phe Gly Asp
465             470               475                   480

His Glu Arg Phe Glu Gln Thr Tyr Phe Ser Thr Phe Lys Asn Met Tyr
                    485               490               495

Phe Ser Gly Asp Gly Ala Arg Arg Asp Glu Asp Gly Tyr Tyr Trp Ile
            500               505               510

Thr Gly Arg Val Asp Asp Val Leu Asn Val Ser Gly His Arg Leu Gly
        515               520               525

Thr Ala Glu Ile Glu Ser Ala Leu Val Ala His Pro Lys Ile Ala Glu
    530               535               540

Ala Ala Val Val Gly Ile Pro His Asn Ile Lys Gly Gln Ala Ile Tyr
545             550               555                   560

Ala Tyr Val Thr Leu Asn His Gly Glu Glu Pro Ser Pro Glu Leu Tyr
                565               570               575

Ala Glu Val Arg Asn Trp Val Arg Lys Glu Ile Gly Pro Leu Ala Thr
            580               585               590

Pro Asp Val Leu His Trp Thr Asp Ser Leu Pro Lys Thr Arg Ser Gly
        595               600               605

Lys Ile Met Arg Arg Ile Leu Arg Lys Ile Ala Ala Gly Asp Thr Ser
    610               615               620

Asn Leu Gly Asp Thr Ser Thr Leu Ala Asp Pro Gly Val Val Glu Lys
625             630               635                   640

Leu Leu Glu Glu Lys Gln Ala Ile Ala Met Pro Ser Gly Asp Pro Asn
                645               650               655

Ser Ser Ser Val Asp Lys Leu Ala Ala Ala Leu Glu His His His His
            660               665               670

His His

<210> SEQ ID NO 11
<211> LENGTH: 338
<212> TYPE: PRT
<213> ORGANISM: Escherichia coli

<400> SEQUENCE: 11

Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
                20                  25                  30

Val Met Val Gly Ile Asp Pro Gln Ser Asp Gly Leu Ala Arg Ala Arg
            35                  40                  45

Arg Met Gly Val Ala Thr Thr His Glu Gly Val Ile Gly Leu Met Asn
        50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140

Arg Val Ala Arg Val His Tyr Ala Glu Ile Ile Ala Ser Ile Ala Ser
```

```
145                 150                 155                 160
Lys Ser Ala Gly Pro Gly Thr Arg Ala Asn Ile Asp Glu Phe Thr Glu
                165                 170                 175

Thr Thr Ser Arg Ala Ile Glu Val Val Gly Gly Ala Ala Lys Gly Lys
            180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
    210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
                245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
    290                 295                 300

Ala Gln Ser Leu Ala Arg Lys Ala Gly Glu Ala Ala Gly Asp Pro Asn
305                 310                 315                 320

Ser Ser Ser Val Asp Lys Leu Ala Ala Ala Leu Glu His His His His
                325                 330                 335

His His
```

SYSTEMS AND METHODS FOR BIOTRANSFORMATION OF CARBON DIOXIDE INTO HIGHER CARBON COMPOUNDS

CROSS-REFERENCE TO RELATED APPLICATION

This application claims the benefit of U.S. Provisional Application No. 61/383,249 filed Sep. 15, 2010, which is expressly incorporated herein by reference in its entirety.

BACKGROUND

As the impending effects of global warming become clearer, there has been an increasing interest in finding ways to reduce our emissions of greenhouse gasses, such a carbon dioxide. While nature has already optimized several routes for converting carbon dioxide into useful compounds, selective pressures in nature are not the same as design parameters for industrial applications.

The idea that proteins are nature's catalysts (enzymes) was born in the early 1800s, and solidified by Payen and Persoz, who are credited as being the first to isolate and characterize an enzyme (amylase, then called diastase). This work demonstrated that an isolated protein could convert starch into sugar (Payen, A., and J. F. Persoz, "Mémoire Sur La Diastase, Les Principaux Produits De Ses Réactions, Et Leurs Applications Aux Arts Industriels," *Annales de Chimie et de Physique* 2:73-92, 1833; Segel, I. H., "Enzyme Kinetics: Behavior and Analysis of Rapid Equilibrium and Steady State Enzyme Systems," New York: Wiley; 1975). Since then over 280 thousand enzymes have been identified, which represent almost 5 thousand different chemical transformations (Chang, A., et al. "BRENDA, AMENDA and FRENDA the Enzyme Information System: New Content and Tools in 2009," *Nucl. Acids Res.* 2008). In addition to the vast chemical space covered by enzymes, they are also some of the world's most efficient catalysts, capable of being either highly regio-stereo-specific (Karsten, W. E., et al., "Kinetic-Studies of L-Aspartase from *Escherichia-Coli*—Substrate Activation," *Biochem.* 25:1299-1303, 1986; Michel, C., et al., "Adenosylcobalamin and Cob(II)Alamin as Prosthetic Groups of 2-Methyleneglutarate Mutase from *Clostridium-Barkeri*," *Eur. J. Biochem.* 205:767-773, 1992) or being relatively non-specific (Coleman, J. E., and P. Gettins, "Alkaline-Phosphatase, Solution Structure, and Mechanism," *Advances in Enzymology and Related Areas of Molecular Biology* 55:381-452, 1983; Sun, H. W., et al., "Enlarging the Substrate Binding Pocket of Yeast Alcohol Dehydrogenase-we," FASEB Journal 5:A1150-A1150, 1991; Green, D. W., et al., "Inversion of the Substrate-Specificity of Yeast Alcohol-Dehydrogenase," *J. Biol. Chem.* 268:7792-7798, 1993; Mast, N., et al. "Broad Substrate Specificity of Human Cytochrome P450 46a1 Which Initiates Cholesterol Degradation in the Brain," *Biochem.* 42:14284-14292, 2003) while catalyzing difficult chemical transformations with rate enhancements of $10^{19}$ in mild and ecologically friendly conditions (Wolfenden, R., and M. J. Snider, "The Depth of Chemical Time and the Power of Enzymes as Catalysts," *Accounts of Chemical Research* 34:938-945, 2001).

Due to this impressive ability to catalyze reactions under mild conditions, enzymes have consistently gained popularity in the fields of industry, medicine, and the basic sciences as tools for performing chemical transformations. One profound example is glucose isomerase, which is currently used in the food industry to produce over a million tons of fructose per year (Powell, K. A., et al., "Directed Evolution and Biocatalysis," *Angewandte Chemie—International Edition* 40:3948-3959, 2001). Yet even with the vast number of enzymes provided by nature, there are numerous important applications for which there is no biological catalyst capable of performing the desired chemical transformation. In order to address these needs, scientists have begun engineering enzymes in order to alter their properties to match the desired need (Ashworth, J., et al. "Computational Redesign of Endonuclease DNA Binding and Cleavage Specificity," *Nature* 441:656-659, 2006; Shah, K., et al., "Engineering Unnatural Nucleotide Specificity for Rous Sarcoma Virus Tyrosine Kinase to Uniquely Label Its Direct Substrates," *Proc. Nat'l Acad. Sci. USA* 94:3565-3570, 1997; Chang, T. K., et al. "Subtiligase: a Tool for Semisynthesis of Proteins," *Proc. Nat'l Acad. Sci. USA* 91:12544-12548, 1994; Jackson, D. Y., et al. "A Designed Peptide Ligase for Total Synthesis of Ribonuclease A With Unnatural Catalytic Residues," *Science* 266:243-247, 1994; Black, M. E., et al. "Creation of Drug-Specific Herpes Simplex Virus Type 1 Thymidine Kinase Mutants for Gene Therapy," *Proc. Nat'l Acad. Sci. USA* 93:3525-3529, 1996; Crameri, A., et al. "Molecular Evolution of an Arsenate Detoxification Pathway by DNA Shuffling," *Nat. Biotechnol.* 15:436-438, 1997; Braha, O., et al. "Designed Protein Pores as Components for Biosensors," *Chem. Biol.* 4:497-505, 1997). While there are examples of success stories, often success is limited by an incomplete understanding of the enzyme's mechanism and the inability to sample the practically limitless number of amino acid sequence combinations from which only a few code for the optimal protein to catalyze the reaction of interest.

Despite the advances in the art regarding modified and optimized enzymes, a need remains for novel enzyme catalysts and methods for their use to convert abundant C1 carbon sources, such as carbon dioxide, into useful hydrocarbons, such as for energy sources. The invention set forth in this disclosure addresses this need and provides further related advantages.

SUMMARY

In one aspect, the invention provides a method for converting formaldehyde to dihydroxyacetone. The method comprises contacting formaldehyde with a thiamine diphosphate cofactor and a polypeptide comprising a motif capable of associating with the thiamine diphosphate cofactor. The motif comprises a histidine residue in a first position, an asparagine or glutamine residue in a second position, and a glutamic acid or aspartic acid residue in a third position. Upon association with the thiamine diphosphate cofactor, the cofactor pyrimidine N1 is hydrogen bonded to the acid side chain of the glutamic acid residue or the acid side chain of the aspartic acid residue of the motif. The histidine N1 and the amide side chain of the asparagine residue or the amide side chain of the glutamine residue are capable of making a water-mediated hydrogen bond with the formaldehyde substrate and/or dihydroxyacetone product.

In some embodiments, the motif is incorporated into a benzaldehyde lyase polypeptide scaffold. In some embodiments, the polypeptide is engineered. In some embodiments, the motif comprises at least one amino acid substitution corresponding to the substitutions selected from the group consisting of A394G, A480W, G419N, A28S, and A28I, with reference to the amino acid sequence set forth in SEQ ID NO:2.

In another aspect, the invention provides an engineered polypeptide to convert formaldehyde to dihydroxyacetone, comprising a motif capable of associating with a thiamine diphosphate carbene cofactor. The motif comprises a histidine residue in a first position, an asparagine or glutamine residue in a second position, and a glutamic acid or aspartic acid residue in a third position. Upon association with the thiamine diphosphate cofactor, the cofactor pyrimidine N1 is hydrogen bonded to the acid side chain of the glutamic acid residue or the acid side chain of the aspartic acid residue of the motif. The histidine N1 and the amide side chain of the asparagine residue or the amide side chain of the glutamine residue are capable of making a water-mediated hydrogen bond with the formaldehyde substrate and/or dihydroxyacetone product.

In some embodiments of the engineered polypeptide, the motif is incorporated into a benzaldehyde lyase polypeptide scaffold. In some embodiments, the motif comprises at least one amino acid substitution corresponding to the substitutions selected from the group consisting of A394G, A480W, G419N, A28S, and A28I, with reference to the amino acid sequence set forth in SEQ ID NO:2.

In another aspect, the invention provides nucleic acid encoding the engineered polypeptide.

In another aspect, the invention provides vector comprising a nucleic acid encoding the engineered polypeptide.

In another aspect, the invention provides a cell transformed with a nucleic acid encoding the engineered polypeptide.

In another aspect, the present invention provides a method for converting formate to formaldehyde. The method comprises: (a) converting formate to formyl CoA by combining formate and Coenzyme A (CoA) with a first enzyme; and (b) forming formaldehyde from the formyl CoA with a second enzyme. In some embodiments, the first enzyme is an acetyl CoA synthase (ACS) or a naturally occurring homolog thereof. In some embodiments, the second enzyme is an acetaldehyde dehydrogenase (ADH) or a naturally occurring homolog thereof.

In another aspect, the invention provides a method for making dihydroxyacetone. The method comprises: (a) converting formate to formyl CoA by combining formate and Coenzyme A (CoA) with a first enzyme; (b) forming formaldehyde from the formyl CoA with a second enzyme; and (c) converting the formaldehyde to dihydroxyacetone with a polypeptide comprising a motif capable of associating with a thiamine diphosphate cofactor. In some embodiments, the first enzyme is an acetyl CoA synthase (ACS) or a naturally occurring homolog thereof. In some embodiments, the second enzyme is an acetaldehyde dehydrogenase (ADH) or a naturally occurring homolog thereof. In some embodiments, the polypeptide motif is incorporated in a benzaldehyde lyase polypeptide scaffold. In some embodiments, the polypeptide is engineered. In some embodiments, the motif comprises at least one amino acid substitution corresponding to the substitutions selected from the group consisting of A394G, A480W, G419N, A28S, and A28I, with reference to the amino acid sequence set forth in SEQ ID NO:2. In some embodiments, the dihydroxyacetone is further converted to a carbon-containing compound suitable for use as a precursor for the generation of a commodity compound.

In another embodiment, the invention provides a method of engineering a polypeptide with activity to convert formaldehyde to dihydroxyacetone. The method comprises: (a) generating a computational model of a complex between an unmodified benzaldehyde lyase polypeptide or naturally occurring homolog thereof, an N-heterocyclic carbene cofactor, and a transition state of the formaldehyde to dihydroxyacetone reaction; (b) identifying at least one candidate peptide residue mutation in the unmodified polypeptide of step (a) predicted to increase the affinity of the motif-cofactor association to the transition state of the formaldehyde to dihydroxyacetone reaction; (c) producing a modified polypeptide comprising the at least one candidate peptide residue mutation identified in step (b); and (d) assaying the modified polypeptide produced in step (c) for activity to convert formaldehyde to dihydroxyacetone.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION

Figure 1:
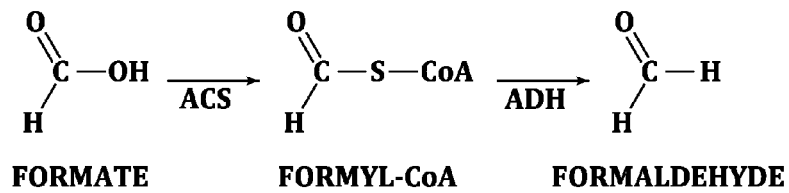
FIG. 1 schematically illustrates the conversion of formate to formyl-CoA by acetyl coenzyme A synthase (ACS), and the subsequent conversion of formyl-CoA to formaldehyde by an acetaldehyde dehydrogenase (ADH).

Unless specifically defined herein, all terms used herein have the same meaning as they would to one skilled in the art of the present invention. Practitioners are particularly directed to Sambrook, et al., *Molecular Cloning: A Laboratory Manual,* 3d ed., Cold Spring Harbor Press, Plainsview, New York (2000), for definitions and terms of the art.

Furthermore, as used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The present invention is based, in part, upon the surprising discovery that a benzaldehyde lyase enzyme (BAL) is able to catalyze the formation of dihydroxyacetone from formaldehyde (i.e. the Formose reaction), a reaction which has no known catalyst. The inventors have also shown that specifically engineered polypeptides based on the BAL scaffold provide enhanced activity and specificity towards the formaldehyde substrate to produce dihydroxyacetone. Furthermore, the inventors have shown that the formaldehyde substrate can be produced upstream of the Formose reaction with the combined use of an acetyl-CoA synthase (ACS) and acylating acetaldehyde dehydrogenase (ADH). Use of these catalysts overcomes a critical technical obstacle to permit the conversion of C1 precursors, such as carbon dioxide, to higher carbon compounds. As used herein, the term "higher carbon compound" refers to molecules containing three or more carbons. The term encompasses sugars, including mono-, di-, and oligo-saccharides, in addition to poly-saccharide compounds. The term also encompasses other higher hydrocarbon compounds. The C3 compounds that can be produced according to the systems and methods of the present invention are useful as precursors for the generation of commodity compounds, because they are be further converted to more complex carbon containing molecules (i.e. with more than 3 carbons), for example, through standard glycolysis reactions.

In accordance with the foregoing, in one an aspect, the present invention provides a method for converting formaldehyde to dihydroxyacetone. A schematic illustration of one embodiment of the reaction is provided in FIG. 2. As illustrated, two C1 formaldehyde molecules are joined to form a C2 intermediate, hydroxyacetaldehyde. An additional formaldehyde molecule is added to form the C3 product, dihydroxyacetone. The reaction of the illustrated embodiment is driven by a formolase (FLS) enzyme, which is described in more detail below. However, this method is not limited to catalysis by FLS, Rather, the present method comprises contacting formaldehyde with an N-heterocyclic carbene cofactor and a polypeptide comprising a motif capable of associating with the N-heterocyclic carbene cofactor.

As used herein, the term "polypeptide" or "protein" are used interchangeably to refer to polymers of amino acids of any length. A polypeptide or amino acid sequence "derived from" a designated protein refers to the origin of the polypeptide. The polypeptide comprises a motif that is capable of associating with an N-heterocyclic carbene cofactor. As used herein, the term "motif" is used to refer to a three dimensional structure appearing in the polypeptide upon proper folding under normal conditions. In some embodiments, the motif comprises less than all amino acid residues present in the polypeptide molecule. In some embodiments, the amino residues comprising the motif do not occupy consecutive residue positions on the polypeptide molecule. However, upon proper folding in a cellular environment, the amino acid residues comprising the motif are positioned in a common three dimensional structure and are capable of acting in concert as an active site. For example, the amino acids of the motif can physically interact, such as forming hydrogen bonds, with a compound that non-covalently occupies three dimensional space defined by the motif. In some embodiments the formation and/or stability of the motif structure is supported by the amino acid residues that lie outside the motif.

In accordance with the present method, the polypeptide comprising a motif is capable of associating with an N-heterocyclic carbene cofactor. As used herein, the term "capable of associating" is used to refer to the ability of the motif to accept and retain the cofactor molecule into the three dimensional space defined by the motif. In some embodiments, the cofactor is stably retained in the motif through the creation of hydrogen bonds. In some embodiments, the association of the motif and the cofactor provides stability to a substrate or product, or transition state to the reaction between the substrate and product. In further embodiments, the interaction facilitates the transformation from the substrate to the product.

In some embodiments of the method, the polypeptide motif comprises a first, second and third amino acid residue position. As used herein, the designations of first, second and third residue positions do not necessarily imply consecutive positions within the primary polypeptide sequence, but can refer to amino acid residue positions that are separated within the sequence by one or more additional residues. Upon proper folding, however, the amino acid residues in the first, second and third positions are disposed within the motif, and thus, within spatial proximity of one another. In some embodiments, the amino acid in the first position is a histidine (H). In some embodiments, the amino acid residue in the second position is an asparagine (N). In other embodiments, the amino acid residue in the second position is a glutamine (Q). In some embodiments, the amino acid residue in the third position is a glutamic acid (E). In other embodiments, the amino acid residue in the third position is an aspartic acid (D). For example, in one embodiment, the amino acid residues in the first, second and third positions are H, N, and E, respectively. In another embodiment, the amino acid residues in the first, second and third positions are H, Q, and E, respectively; the amino acid residues in the first, second and third positions are H, N, and D, respectively; or the amino acid residues in the first, second and third positions are H, Q, and D, respectively. In one embodiment, the first, second, and third amino acid residue positions correspond to amino acid residues sequence positions 29, 113, and 50, respectively, of the benzaldehyde lyase polypeptide sequence set forth herein as SEQ ID NO:2

In some embodiments, the N-heterocyclic carbene cofactor is thiamine diphosphate. In other embodiments, the N-heterocyclic carbene cofactor is an imidazolylidenes. As used herein, the term "imidazolylidenes" refers to a compound with a 5-member ring based on imidazole, often with the nitrogen atoms in the imidazole structure being methylated or bearing other substituents allowing the carbene to form at the C2 position. In other embodiments, the N-heterocyclic carbene cofactor is thiazole.

In some embodiments, upon association of the motif with the N-heterocyclic carbene cofactor, a nitrogen atom of the cofactor heterocyclic ring forms a hydrogen bond with the side chain of an amino acid residue of the motif. The term "hydrogen bond" refers to the attractive interaction between the hydrogen bound to one electronegative atom with another electronegative atom from another molecule or chemical group. In some embodiments, upon association of the motif with the cofactor, the hydrogen bond is formed with the acid side chain of a glutamic acid residue in the third residue position. In other embodiments, upon association of the motif with the cofactor, the hydrogen bond is formed with the acid side chain of an aspartic acid residue in the third residue position.

In some embodiments, the N-heterocyclic carbene cofactor is thiamine diphosphate. Upon association of the motif with the thiamine diphosphate cofactor molecule, the N1 atom of the cofactor pyrimidine ring is capable of forming a hydrogen bond with the side chain of an amino acid residue of the motif. In some embodiments, the N1 atom of the thiamine diphosphate cofactor pyrimidine ring is hydrogen bonded with the acid side chain of the residue in the third position. In some embodiments, the N1 atom of the cofactor pyrimidine ring is hydrogen bonded with the acid side chain of the glutamic acid residue in the third position. In other embodiments, the N1 atom of the cofactor pyrimidine ring is hydrogen bonded with the acid side chain of the aspartic acid residue in the third position.

In some embodiments, the amino acid in the first position is a histidine (H) and is capable of forming a water-mediated hydrogen bond with the formaldehyde substrate and/or dihydroxyacetone product, or any intermediate created in the conversion of formaldehyde to dihydroxyacetone. The term "water-mediated hydrogen bond" refers to the general attraction between two chemical groups, wherein each group forms a hydrogen bond with the same water molecule that is disposed between the two groups. In further embodiments, the N1 atom of the histidine imidazole ring structure is capable of forming a water-mediated hydrogen bond with the formaldehyde substrate and/or dihydroxyacetone product, or any intermediate created in the conversion of formaldehyde to dihydroxyacetone.

In some embodiments, the side chain of the amino acid residue in the second position is capable of forming a water-mediated hydrogen bond with the formaldehyde substrate and/or dihydroxyacetone product, or any intermediate created in the conversion of formaldehyde to dihydroxyacetone. In some embodiments, the residue in the second amino acid position has an amide side chain that is capable of forming the water-mediated hydrogen bond. In some embodiments, the amino acid residue in the second position is an asparagine residue, wherein the amide side chain is capable of forming a water-mediated hydrogen bond with the formaldehyde substrate and/or dihydroxyacetone product, or any intermediate created in the conversion thereof. In other embodiments, the amino acid residue in the second position is a glutamine residue, wherein the amide side chain is capable of forming a water-mediated hydrogen bond with the formaldehyde substrate and/or dihydroxyacetone product, or any intermediate created in the conversion thereof.

In some embodiments, the N1 atom of the histidine imidazole ring structure (in the first residue position) and the amide side chain of the asparagine residue or the amide side chain of the glutamine residue (in the second residue position) are capable of simultaneously making a water-mediated hydrogen bond with the formaldehyde substrate and/or dihydroxyacetone product, or any intermediate in the conversion thereof.

Figure 5:
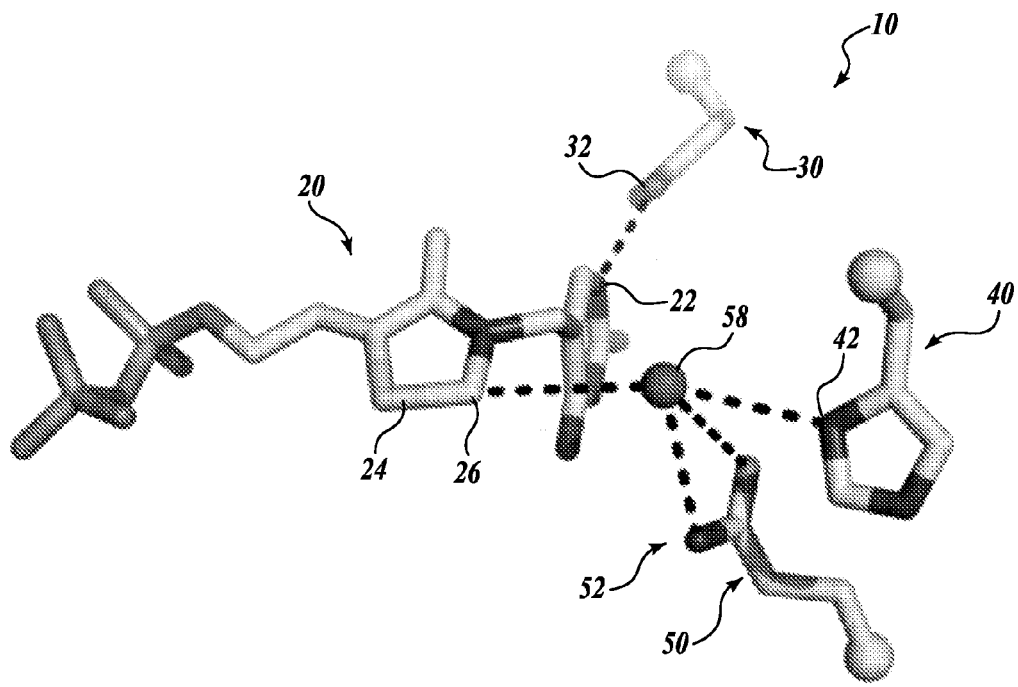
FIG. 5 is a three dimensional stick model of a motif of the present invention in association with a thiamine diphosphate cofactor, which, are capable of catalyzing the conversion of formaldehyde to dihydroxyacetone. The dotted lines indicate distances of up to 4.5 angstroms.

FIG. 5 illustrates a three-dimensional stick model of one embodiment of the association 10 between the motif and N-heterocyclic carbene cofactor provided by the present invention. In this illustrative embodiment, the N-heterocyclic carbene cofactor is thiamine diphosphate 20. The N1 atom 22 of the cofactor pyrimidine is hydrogen bonded to the acid side chain 32 of the amino acid in the third residue position 30. In the illustrated embodiment, the amino acid in the third residue position 30 is a glutamic acid residue. A histidine residue is in the first amino acid residue position 30. The N1 atom 42 of the histidine imidazole ring structure is hydrogen bonded with a water molecule 58. The amino acid residue in the second position 50, illustrated as a glutamine residue, has an amide side chain 52. The amide side chain 52 of the glutamine residue is hydrogen bonded with the water molecule 58. In the illustrated embodiment, the dashed lines represent distances ranging between 3.5 to 4.5 angstroms. For example, as illustrated, the C2 carbene 26 of the thiamine diphosphate 20 thiazole ring 24 is between 3.5 to 4.5 angstroms from the water molecule 58.

In some embodiments, the motif is incorporated in a benzaldehyde lyase polypeptide scaffold. As used herein, the term "scaffold" refers the three-dimensional structure provided by the non-motif amino acid residues in the polypeptide that facilitates the formation and stability of the motif contained therein. As discussed below and in Example 1, the present inventors made the surprising discovery that a benzaldehyde (BAL) from *Pseudomonas fluorescens* can catalyze the conversion of formaldehyde to dihydroxyacetone. See FIG. 4. Accordingly, in some embodiments, the BAL polypeptide scaffold comprises an amino acid sequence set forth herein as SEQ ID NO:2. The inventors also discovered that a BAL homolog, Genbank accession number NP_945464.1, with an amino acid sequence set forth herein as SEQ ID NO:3, also exhibits activity in the conversion of formaldehyde to dihydroxyacetone. This homolog has approximately 40% identity with the BAL represented by SEQ ID NO:2, indicating that a wide variety of variation is possible in the BAL scaffold and still retain the ability to support a motif/cofactor association that can function according the methods of the invention. Accordingly, in some embodiments, the BAL polypeptide scaffold comprises an amino acid sequence with approximately 40%, 45%, 50%, 55%, 60%, 65%, 70%, 75%, 80%, 85%, 90%, 95%, or 99% identity to the amino acid sequence set forth herein as SEQ ID NO:2. As used herein, the term "percent identity" or "percent identical", refers to the percentage of amino acid residues in a polypeptide sequence that are identical with the amino acid sequence of a specified molecule, after aligning the sequences to achieve the maximum percent identify. For example, Vector NTI Advance™ 9.0 may be used for sequence alignment. Alignments may include the introduction of gaps in the sequences to be aligned to maximize the percent identity. However, regardless of the variation permitted in these embodiments, the scaffold must support the structure of the first, second, and third amino acid residue positions.

In some embodiments, the polypeptide is engineered. Therefore, in these embodiments, the present invention provides a method for converting formaldehyde to dihydroxyacetone, comprising contacting formaldehyde with an engineered polypeptide. As used herein, the term "engineered" refers to a polypeptide that does not occur in nature, but was designed and/or produced with modifications that facilitate or enhance the catalytic properties of the motif. In some embodiments, the engineered polypeptide contains mutations intended to modify the structure and catalytic capabilities of the polypeptide. The engineered polypeptide may be produced by any suitable method. For example, the polypeptide can be encoded by a experimentally mutated gene that is transgenically expressed in a host cell, as described below. Alternatively, the polypeptide may be synthesized. In this regard, fragments of approximately 20 amino acids can be synthesized by known means and conjugated into a longer polypeptide macromolecule and permitted to fold in suitable conditions that are known in the art.

In some embodiments, the motif comprises at least one amino acid substitution in reference to the BAL scaffold sequence, as set forth in SEQ ID NO:2. Terminology used to describe substitution mutations are described in terms of a reference sequence, such as the BAL scaffold sequence, as set forth in SEQ ID NO:2. This terminology first identifies the reference (wild type) amino acid residue, then identifies the amino acid residue position in the linear/primary reference amino acid sequence starting from the amino (N)-terminus, and finally identifies the new amino acid residue introduced via the substitution. According to this terminology, in some embodiments, the motif comprises at least one amino acid substitution selected from the group consisting of A394G, A480W, G419N, A28S, and A28I, with reference to the BAL scaffold sequence, as set forth in SEQ ID NO:2. Embodiments include motifs comprising one, two, three, and four of the indicated amino acid substitutions, in any possible combination. In some embodiments, the motif comprises the amino acid substitutions corresponding to A394G and A480W, with reference to the amino acid sequence set forth in SEQ ID NO:2. As used herein, the term "formolase" refers to an engineered enzyme or polypeptide scaffold containing at least one amino acid substitution and has catalytic activity in the conversion of formaldehyde to dihdroxyacetone.

The inventors have shown that an engineered enzyme with substitutions A28S, A394G, and A480W, referred to below as formolase r3a, has catalytic activity in the conversion of formaldehyde to dihdroxyacetone. See TABLE 1. The amino acid sequence of engineered formolase r3a is set forth herein as SEQ ID NO:4. Accordingly, In some embodiments, the benzaldehyde lyase polypeptide scaffold comprises an amino acid sequence with approximately 40%, 45%, 50%, 55%, 60%, 65%, 70%, 75%, 80%, 85%, 90%, 95%, or 99% identity to the amino acid sequence set forth herein as SEQ ID NO:4. In some embodiments, the benzaldehyde lyase polypeptide scaffold comprises an amino acid sequence set forth in SEQ ID NO:4.

The inventors have shown that engineered enzymes with three substitutions selected from A394G, A480W, G419N, A28S, in all combinations, referred to below as formolase r3a-d, have catalytic activity in the conversion of formaldehyde to dihdroxyacetone. See TABLE 1. The amino acid sequences of engineered formolase r3a-d are set forth herein as SEQ ID NOS:4, 5, 6, and 7, respectively. Accordingly, in some embodiments, the motif comprises at least three amino acid substitutions corresponding to the substitutions selected from the group consisting of A394G, A480W, G419N, A28S, and A28I, with reference to the amino acid sequence set forth in SEQ ID NO:2. In some embodiments, the benzaldehyde lyase polypeptide scaffold comprises an amino acid sequence with approximately 40%, 45%, 50%, 55%, 60%, 65%, 70%, 75%, 80%, 85%, 90%, 95%, or 99% identity to any one of the amino acid sequences set forth herein as SEQ ID NOS:4, 5, 6, or 7. In some embodiments, the benzaldehyde lyase polypeptide scaffold comprises any one of the amino acid sequences set forth in SEQ ID NOS:4, 5, 6, or 7.

The inventors have shown that engineered enzymes with four substitutions, A394G, A480W, G419N, A28S, or four substitutions, A394G, A480W, G419N, A28I, referred to below as formolase r4a and r4b, respectively, have catalytic activity in the conversion of formaldehyde to dihdroxyacetone. See and TABLE 1. The amino acid sequences of engineered formolase r4a and r4b are set forth herein as SEQ ID NOS:8 and 9, respectively. Accordingly, in some embodiments, the motif comprises at least 4 amino acid substitutions corresponding to the substitutions selected from the group consisting of A394G, A480W, G419N, A28S, and A28I, with reference to the amino acid sequence set forth in SEQ ID NO:2. In some embodiments, the benzaldehyde lyase polypeptide scaffold comprises an amino acid sequence with approximately 40%, 45%, 50%, 55%, 60%, 65%, 70%, 75%, 80%, 85%, 90%, 95%, or 99% identity to any one of the amino acid sequences set forth herein as SEQ ID NOS:8 and 9. In some embodiments, the benzaldehyde lyase polypeptide scaffold comprises any one of the amino acid sequences set forth in SEQ ID NOS:8 and 9.

In another aspect, the present invention provides an engineered polypeptide as described above. The engineered polypeptide comprises a motif capable of associating with an N-heterocyclic carbene cofactor. In some embodiments, the motif is incorporated into a BAL scaffold. It will be apparent to a skilled practitioner that, as an engineered polypeptide, the scaffold or motif comprises at least one mutation from the wild type BAL sequence, such as the sequence set forth in SEQ ID NO:2. The mutation can be a substitution, deletion, or insertion of one or more amino acid residues.

As described above, in some embodiments of this aspect, the motif comprises a histidine residue in a first position, an asparagine or glutamine residue in a second position, and a glutamic acid or aspartic acid residue in a third position. In some embodiments of this aspect, upon association with the N-heterocyclic carbene cofactor, a cyclic N atom of the cofactor is hydrogen bonded with the acid side chain of the glutamic acid residue or the acid side chain of the aspartic acid residue of the motif.

In some embodiments, the N-heterocyclic carbene cofactor is thiamine diphosphate, and upon association with the cofactor, the cofactor pyrimidine N1 is hydrogen bonded to the acid side chain of the glutamic acid residue or the acid side chain of the aspartic acid residue of the motif.

In some embodiments, the histidine N1 in the first residue position and the amide side chain of an asparagine residue or the amide side chain of a glutamine residue in the second residue position are capable of making a water-mediated hydrogen bond with the formaldehyde substrate and/or dihydroxyacetone product.

As described above, in some embodiments, the engineered polypeptide motif comprises at least one amino acid substitution corresponding to the substitutions selected from the group consisting of A394G, A480W, G419N, A28S, and A28I, with reference to the amino acid sequence set forth in SEQ ID NO:2. In some embodiments, the motif can comprise one, two, three, or four of the substitutions selected from the group consisting of A394G, A480W, G419N, A28S, and A28I, with reference to the amino acid sequence set forth in SEQ ID NO:2. In some embodiments, the benzaldehyde lyase polypeptide scaffold comprises an amino acid sequence with 40%, 45%, 50%, 55%, 60%, 65%, 70%, 75%, 80%, 85%, 90%, 95%, or 99% identity to any one of the amino acid sequences set forth herein as SEQ ID NOS:2 and 4-9.

In some embodiments, the motif of the engineered polypeptide, when in association with the N-heterocyclic carbene cofactor, converts or catalyzes the conversion of formaldehyde to dihydroxyacetone with a $k_{cat}/K_m$ constant of at least 0.2 $M^{-1}s^{-1}$ under suitable conditions. An illustrative embodiment of an assay to establish the $k_{cat}/K_m$ of the reaction is described below and in Example 3.

In another aspect, the present invention provides a motif that is capable of associating with an N-heterocyclic carbene cofactor to convert formaldehyde to dihydroxyacetone. As described above, in some embodiments of this aspect, the motif comprises a histidine residue in a first position, an asparagine or glutamine residue in a second position, and a glutamic acid or aspartic acid residue in a third position.

In some embodiments of this aspect, upon association with the N-heterocyclic carbene cofactor, a cyclic N atom of the cofactor is hydrogen bonded with the acid side chain of the glutamic acid residue or the acid side chain of the aspartic acid residue of the motif. In some embodiments, the N-heterocyclic carbene cofactor is thiamine diphosphate, and upon association with the cofactor, the cofactor pyrimidine N1 is hydrogen bonded to the acid side chain of the glutamic acid residue or the acid side chain of the aspartic acid residue of the motif.

In some embodiments, the histidine N1 in the first residue position and the amide side chain of an asparagine residue or the amide side chain of a glutamine residue in the second residue position are capable of making a water-mediated hydrogen bond with the formaldehyde substrate and/or dihydroxyacetone product.

As described above in context of the engineered polypeptide, in some embodiments, the motif comprises at least one amino acid substitution corresponding to the substitutions selected from the group consisting of A394G, A480W, G419N, A28S, and A28I, with reference to the amino acid sequence set forth in SEQ ID NO:2.

In some embodiments, the motif is engineered.

In another aspect, the present invention provides a nucleic acid encoding an engineered polypeptide, as described above. In some embodiments, the nucleic acid contains nucleotide sequence modifications to reflect the codon bias of a particular expression system or cell.

In another aspect, the present invention provides a vector comprising a nucleic acid encoding an engineered polypeptide, as described above. As used herein, the term "vector" is a nucleic acid molecule, preferably self-replicating, which transfers and/or replicates an inserted nucleic acid molecule into and/or between host cells. In some embodiments, the vector includes a nucleic acid sequences allowing for autonomous replication, which refers to a polynucleotide comprising an origin of replication (generally referred to as an on sequence) that allows for replication of the polynucleotide in the appropriate host cell. In some embodiments, the vector includes a nucleic acid sequences allowing for selection, which refers to polynucleotides encoding any protein that provides a phenotypic marker. Embodiments include such markers as, for example, a protein that is necessary for cell growth, resistance to a toxin, and a protein providing a surface antigen for which specific antibodies/ligands are available. Non-limiting examples include amino acid biosynthetic genes, the URA3 gene, or reporter genes that encode proteins detectable by a suitable assay.

In another aspect, the present invention provides a cell comprising the nucleic acid and/or vector described above. In some embodiments, the cell has been transformed with the nucleic acid and/or vector described above. In some embodiments, the cell is the progeny of a cell that was transformed with the nucleic acid and/or vector described above. In some embodiments, the cell is prokaryotic, such as a gram negative or a gram positive bacterium. For example, as described below, the engineered formolase polypeptides were transformed into the BL21(DE3) strain of E. coli. In some embodiment, the cell is eukaryotic, such as cells derived from fungus, plants, insects, amphibians, or mammals.

In another aspect, the present invention provides a method of making an engineered polypeptide, as described above. The method comprises generating a nucleic acid sequence encoding the described engineered polypeptide. The nucleic acid may be derived from the wild type nucleic acid encoding a BAL polypeptide. An illustrative nucleic acid sequence encoding a BAL polypeptide is set forth herein as SEQ ID NO:1, which encodes the amino acid sequence set forth in SEQ ID NO:2. SEQ ID NO:1 is an artificial nucleic acid sequence that was synthesized from small oligos based on *Pseudomonas fluorescens* polypeptide sequence, but the sequences used vary from the naturally occurring sequence to optimize for codon usage and expression E. coli. The synthesized, optimized BAL sequence was expressed in E. coli in a manner that also incorporated a HIS tag sequence to facilitate its purification.

Modifications to the nucleic acid sequence that result in amino acid substitutions can be performed using any suitable techniques known in the art. An illustrative example is the Kunkel mutagenesis method, as described in more detail in Example 2. Briefly, a nucleic acid primer is generated that contains the desired nucleic acid mutation. The mutation has flanking nucleic acid regions are complementary to the wild type nucleic acid sequences that flank the target site. For example, the mutations generated as described in Example 2 utilized primers that annealed to sections of SEQ ID NO:1 that contained the encoded mutation in the appropriate site, but retaining complementary to SEQ ID NO:1 at the 3' and 5' ends relative to the mutation. Upon annealing, the complementary strand of DNA is elongated. The resulting DNA strand, and/or any replicate thereof, that contains the mutation can be ligated into an expression vector and transformed into a cell. The cell is made to express the polypeptide comprising the one or more substitutions, which can then be isolated or purified in its properly folded form using standard techniques.

In another aspect, the present invention provides a method of engineering a polypeptide with activity to convert formaldehyde to dihydroxyacetone. The method comprises generating a computation model of a complex between a BAL polypeptide, an N-heterocyclic carbene cofactor, and a transition state of the formaldehyde to dihydroxyacetone reaction.

In some embodiments, the BAL polypeptide is an unmodified, or wild type BAL polypeptide. In other embodiments, the BAL polypeptide sequence contains introduced insertions, deletions or substitutions. However, mutations notwithstanding, the sequence and three dimensional structure are known. In yet further embodiments, the polypeptide is a naturally occurring homolog of a BAL enzyme. A representative list of BAL homologs is provided in Table 3, which lists the Genbank accession numbers for each homolog.

In some embodiments, the N-heterocyclic carbene cofactor is thiamine diphosphate. In other embodiments, the N-heterocyclic carbene cofactor is an imidazolylidene. In other embodiments, the N-heterocyclic carbene cofactor is thiazole.

As described below, it has been theorized that an enzyme's proficiency is proportional to its affinity towards the transition state (TS) of the reaction. As used herein, the term "transition state" refers to the chemical conformation during a reaction corresponding to the highest energy state of the reaction components. Often, chemical reactions, such as the conversion of formaldehyde to dihydroxyacetone, are considered to have multiple transition states, or conformations with high energy states. These TSs are preceded and followed by conformations of lower energy.

In some embodiments, the computational model is generated by a suitable computer software program. Representative examples of computer software used to create three dimensional structural models of polypeptide complexes include DEZYMER, ORBIT, and the ROSETTA program suite, including ROSETTA, ROSETTADESIGN, and ROSETTALIGAND, as described below. To generate the computational model, the three dimensional structure of the BAL polypeptide, or homolog thereof, the N-heterocyclic carbene cofactor, and the chemical conformation representing TS of the formaldehyde to dihydroxyacetone reaction are input. Based on this input data, a complex model is generated computationally.

Based on the generated complex, at least one candidate peptide residue mutation in the modeled polypeptide is identified that is predicted to increase the stability of the polypeptide/cofactor complex. The increased stability theorized to support the TS of the formaldehyde to dihydroxyacetone reaction. Without being bound by any particular theory, a predicted increased stability indicates that the polypeptide/cofactor complex has a greater ability to stabilize the reaction TS, resulting in a reduced energy of the transition and a higher likelihood that the substrate compounds will progress through the reaction to form the substrate (i.e. dihydroxyacetone). The candidate peptide residue mutation can be a deletion, insertion, or substitution. In some embodiments, more than one mutation is predicted to increase the affinity of the motif-cofactor association to the TS of the formaldehyde to dihydroxyacetone reaction.

The present method further comprises producing an engineered or modified polypeptide comprising the at least one candidate peptide residue mutation identified based on the computational model. The step of producing an engineered or modified polypeptide can be accomplished according to the description provided herein.

The resulting engineered or modified polypeptide is assayed for catalytic activity to convert formaldehyde to dihydroxyacetone. In some embodiments, the activity of the engineered polypeptide is assayed by the spectrophotometric observation at 340 nM of NADH consumption that occurs in a coupled reaction, wherein the dihydroxyacetone is further reduced to glycerol by glycerol dehydrogenase in a non-limiting step. An embodiment of this assay is described in Example 1. In some embodiments, the modified polypeptide comprising the at least one peptide residue mutation has an increased activity to convert formaldehyde to dihydroxyacetone compared to the unmodified polypeptide.

As described below, the inventors have also shown that the formaldehyde substrate for the Formose reaction can be generated using polypeptide catalysts not previously known for this ability or purpose. Accordingly, in another aspect, the invention provides a method for converting formate to formaldehyde.

The method comprises a first step of converting formate to formyl CoA by combining formate and Coenzyme A (CoA) with a first enzyme. The first enzyme is capable of combining a carboxylic acid and CoA to provide an acyl-CoA product. In some embodiments, this reaction step utilizes the energetic release provided by ATP hydrolysis. In some embodiments, the first enzyme is an acetyl CoA synthase (ACS). A representative ACS is derived from E. coli, and is known to facilitate replacement of the hydroxyl group of acetate with the CoA using the energetic release provided by hydrolysis of ATP. An amino acid sequence of a representative ACS is set forth herein as SEQ ID NO:10. In some embodiments, the first enzyme is a naturally occurring homolog of an ACS. In some embodiments, the first enzyme comprises an amino acid sequence that has 40%, 45%, 50%, 55%, 60%, 65%, 70%, 75%, 80%, 85%, 90%, 95%, or 99% identity to SEQ ID NO:10. In some embodiments, the first enzyme is an engineered enzyme that comprises at least one amino acid residue mutation in reference to the sequence of any one of the embodiments described above in this paragraph. The engineered first enzyme can be designed and produced according to the methods described supra, in context of the engineered polypeptide to convert formaldehyde to dihydroxyacetate. The amino acid residue mutation can be a deletion, addition, or substitution.

The method also comprises a second step of forming formaldehyde from the formyl CoA with a second enzyme. The second enzyme is capable of catalyzing the reduction of an acyl-CoA to provide an aldehyde product. In some embodiments, this reduction step utilizes NADH or NADPH as the reducing agent. In some embodiments, the second enzyme is an acetaldehyde dehydrogenase (ADH). A representative ADH is derived from E. coli, and is known to facilitate reduction of the "activated" acyl-CoA to provide acetaldehyde using NADH as the reducing agent. An amino acid sequence of a representative ACS is set forth herein as SEQ ID NO:11. In some embodiments, the second enzyme is a naturally occurring homolog of an ADH. In some embodiments, the second enzyme comprises an amino acid sequence that has 40%, 45%, 50%, 55%, 60%, 65%, 70%, 75%, 80%, 85%, 90%, 95%, or 99% identity to SEQ ID NO:11. In some embodiments, the second enzyme is an engineered enzyme that comprises at least one amino acid residue mutation in reference to the sequence of any one of the embodiments described above in this paragraph. The engineered second enzyme can be designed and produced according to the methods described supra, in context of the engineered polypeptide to convert formaldehyde to dihydroxyacetate. The amino acid residue mutation can be a deletion, addition, or substitution.

FIG. 1 schematically illustrates an embodiment of the formate to formaldehyde conversion provided by the present invention. In this embodiment, formate is converted to an acyl-CoA (i.e., formyl CoA) by ACH in a first step. In the second step, the formyl-CoA is reduced to formaldehyde by ADH.

In some embodiments, the method is performed in a single reaction cascade and or/under the same reaction conditions. A description of illustrative reaction conditions is provided in Example 4. In other embodiments, the first and second steps of the method are performed in discrete reactions and/or under distinct reaction conditions.

As will be apparent to persons of ordinary skill in the art, the progress of the reaction, or reaction steps, can be monitored by the consumption of ATP and/or NADH, according the known methods. A description of a representative assay is provided in Example 4.

In another aspect, the invention provides a method of making dihydroxyacetone. In a first step, the method comprises converting formate to formyl CoA using the methods and compounds described above. In a second step, the method comprises converting the formyl CoA to formaldehyde using the methods and compounds described above. In a third step, the method comprises converting the formaldehyde to dihydroxyacetone with a polypeptide using the methods and compounds described above.

Figure 3:
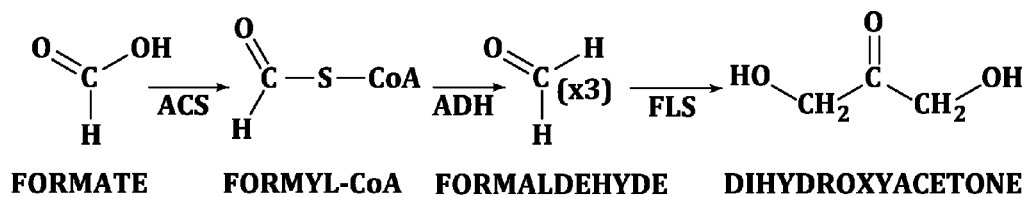
FIG. 3 schematically illustrates the production of dihydroxyacetone from the formate substrate, wherein formate is converted to formyl-CoA by acetyl coenzyme A synthase (ACS), formyl-CoA is converted to formaldehyde by acetaldehyde dehydrogenase (ADH), and formaldehyde is converted to dihydroxyacetone by an engineered formolase (FLS).

In some embodiments, the steps of the methods are performed separately and/or under distinct conditions. In other embodiments, the steps of the method are performed in a single reaction cascade. FIG. 3 schematically represents an illustrative embodiment of the formate to dihydroxyacetone conversion provided by the invention. In this embodiment, formate is converted to an acyl-CoA (i.e., formyl CoA) by an ACH in a first step. In the second step, the formyl-CoA is reduced to formaldehyde by an ADH. In the third step, three formaldehyde molecules are converted to dihydroxyacetone by an FLS.

In some embodiments, the formate used as the substrate for the method is produced from carbon dioxide. In some embodiments, the carbon dioxide is converted to formate using an enzymatic catalyst. In some embodiments, the enzymatic catalyst is a formate dehydrogenase (FDH). An exemplary FDH is described below, and converts carbon dioxide to formate using NADH or NADPH as the reducing agent. In some embodiments the enzymatic catalyst is a naturally occurring homolog of an FDH.

In some embodiments, the carbon dioxide is converted to formate without an enzymatic catalyst. For example, formate can be produced by applying electrical current to water containing carbon dioxide and lead (Li, H. and Oloman, C., "The Electro-Reduction of Carbon Dioxide in a Continuous Reactor," *Journal of Applied Electrochemistry* 35:955-965, 2005).

In some embodiments, the dihydroxyacetone is further used as a substrate to produce a commodity compound. As used herein, the term "commodity compound" refers to any saleable or useful carbon-containing compound. As described herein, the use of the methods and compounds of the invention results in the production of dihydroxyacetone. Dihydroxyacetone is a C3 compound and provides a convenient an entry point to known glycolysis pathways. For example, dihydroxyacetone can be converted through existing cellular glycolysis pathway into acetyl-CoA, without additional modification of the cell. Thus, prokaryotic or eukaryotic cells or cell systems can be applied to convert dihydroxyacetone into acetyl-CoA. Acetyl-CoA is a central metabolic building block for the glycolysis pathway, and as such, is a common precursor that can be used for the downstream production of many commodity compounds by methods known in the art. Examples of commodity compounds are compounds useful in industrial processes, such as tanning agents, and biofuel compounds. As used herein, the term "biofuel" includes solid, liquid, or gas fuels derived, at least in part, from a biological source, such as a recombinant microorganism. Examples of commodity compounds including biofuels, and methods of their generation through glycolysis-related pathways are described in U.S. patent application Ser. No. 12/245,540 (Publication number US 2009/0155873 A1), which is explicitly incorporated herein by reference.

The following is a description of a representative method to engineer a polypeptide to convert formaldehyde to dihydroxyacetone, and methods of its use in systems to transform carbon dioxide into sugars.

A. Establishing Benzaldehyde Lyase (BAL) as a Polypeptide Scaffold for the Catalytic Conversion of Formaldehyde to Dihydroxyacetone Existing biochemical pathways are known that are capable of converting carbon dioxide into methanol (Obert, R., and B. C. Dave, "Enzymatic Conversion of Carbon Dioxide to Methanol: Enhanced Methanol Production in Silica Sol-Gel Matrices," *J. Am. Chem. Soc.* 121:12192-12193, 1999). While methanol is useful as a C1 compound, a major interest also lies in compounds larger than C1. The natural pathway for converting C1 compounds into larger molecules is complex and has not been successfully translated into commercial applications utilizing either the native hosts or more common hosts such as *Escherichia coli* or *Saccaromyces cerevisiae* (Lidstrom, M. E., and D. I. Stirling, "Methylotrophs: Genetics and Commercial Applications," *Ann. Rev. Microbiol.* 44:27-58, 1990). Accordingly, aspects of the disclosure are directed toward engineering a new pathway in which C1 compounds can be utilized (e.g., conversion of $CO_2$ into a central metabolic intermediate) such that many new materials that were previously unobtainable through traditional C1 pathways are now accessible (Fortman, J. L., et al., "Biofuel Alternatives to Ethanol: Pumping the Microbial Well," *Trends in Biotechnology* 26:375-381, 2008; Nakamura, C. E., and G. M. Whited, "Metabolic Engineering for the Microbial Production of 1,3-Propanediol," Curr. Opin. *Biotech.* 14:454-459, 2003; Ro, D. K., et al., "Production of the Antimalarial Drug Precursor Artemisinic Acid in Engineered Yeast," *Nature* 440:940-943, 2006). Specifically, the present disclosure focuses on one intermediate, formaldehyde.

Formaldehyde is a highly reactive molecule (Peeters, D., and G. Leroy, "A Theoretical Approach to the Acid-Catalyzed Hydration of the Carbonyl Group—the Case of Formaldehyde," *Canadian Journal of Chemistry-Revue Canadienne De Chimie* 69:1376-1387, 1991), known to self polymerize into carbohydrates in the presence of a concentrated base (Matsumoto, T., et al., "Selective Formation of Triose From Formaldehyde Catalyzed by Thiazolium Salt," *J. Am. Chem. Soc.* 106:4829-4832, 1984). This polymerization reaction is known as the Butlerov or Formose reaction (Simonov, A., et al., "The Nature of Autocatalysis in the Butlerov Reaction," *Kinetics and Catalysis* 48:245-254, 2007; Breslow, R., "On the Mechanism of the Formose Reaction," *Tetrahedron Letters* 1:22-26, 1959). Therefore, as disclosed herein, an enzyme capable of catalyzing a Formose reaction, such as trimerizing formaldehyde (a C1 compound) into dihydroxyacetone (a C3 compound), creates an entry point for C1 compounds, such as $CO_2$, into glycolysis. While the existence of an enzyme capable of catalyzing Formose reactions has been theorized, most reports refute the existence of such an enzyme (W.E.F., "The Supposed Presence of Formaldehyde-Polymerizing Enzyme in Green Leaves," *New Phytologist* 44:17-24, 1945). To date no one has reported an enzyme capable of ligating three formaldehydes to form the small sugar dihydroxyacetone.

Numerous bases catalyze the Formose reaction. One such class of bases are thiazolium salts (Matsumoto, T., et al., "Selective Formation of Triose From Formaldehyde Catalyzed by Thiazolium Salt," *J. Am. Chem. Soc.* 106:4829-4832, 1984). A thiazolium derivative, thiamine pyrophosphate (ThDP, the active form of Vitamin B1), is a ubiquitous enzyme cofactor (Breslow, R., "On the Mechanism of Thiamine Action. IV.1 Evidence from Studies on Model Systems," *J. Am. Chem. Soc.* 80:3719-3726, 1958; Pohl, M., et al., "A New Perspective on Thiamine Catalysis," *Curr. Opin. Biotech.* 15:335-342, 2004). Therefore, enzymes that utilize this cofactor were considered as preliminary targets to investigate potential catalytic effect for the Formose reaction. In particular, the enzyme Benzaldehyde Lyase (BAL), isolated recently from *Pseudomonas fluorescens* biovar we (Gonzalez, B., and R. Vicuna, "Benzaldehyde Lyase, a Novel Thiamine PPI-Requiring Enzyme, from *Pseudomonas-Fluorescens* Biovarwe," *J. Bacteriol.* 171:2401-2405, 1989), has been shown to be a highly efficient catalyst for the Benzoin Reaction in which two benzaldehydes are ligated to form a single benzoin molecule (Zavrel, M., et al., "Mechanistic Kinetic Model for Symmetric Carboligations Using Benzaldehyde Lyase," *Biotech. and Bioeng.* 101:27-38, 2008). Through specificity and kinetic studies, it has been shown that the phenyl rings of benzaldehyde are not essential to this enzymatic reaction, making BAL capable of ligating many different aldehydes to form alpha-hydroxy ketones (Janzen, E., et al., "Characterization of Benzaldehyde Lyase From *Pseudomonas Fluorescens*: a Versatile Enzyme for Asymmetric C—C Bond Formation," *Bioorganic Chem.* 34:345-361, 2006; Chakraborty, S., et al., "Mechanism of Benzaldehyde Lyase Studied via Thiamin Diphosphate-Bound Intermediates and Kinetic Isotope Effects," *Biochem.* 47:3800-3809, 2008). However, a review of the literature indicates that BAL has not been tested for activity with formaldehyde.

To test BAL for activity with formaldehyde, the *E. coli* optimized gene coding for BAL (Hoover, D. M., and J. Lubkowski, "DNAWorks: An Automated Method for Designing Oligonucleotides for PCR-Based Gene Synthesis," *Nucl. Acids Res.* 30:e43, 2002) was synthesized and cloned into an expression vector (pET29b+ from Novagen) containing a His-Tag for subsequent Immobilized Metal Affinity Chromatography (IMAC) purification (Consortium, S. G., et al., "Protein Production and Purification," *Nat. Meth.* 5:135-146, 2008; Porath, J., "Immobilized Metal Ion Affinity Chromatography," *Protein Expression and Purification* 3:263-281, 1992). The amino acid sequence for the BAL polypeptide is set forth herein as SEQ ID NO:2, encoded by the nucleic acid sequence set forth herein as SEQ ID NO: 1. Protein was produced and purified by transforming the vector into BL21 (DE3) (Novagen Cat. No. 69450). The protein was overexpressed via auto-induction (Studier, F. W., "Protein Production by Auto-Induction in High-Density Shaking Cultures," *Protein Expression and Purification* 41:207-234, 2005) and IMAC purified. The purity of the appropriately sized protein was subsequently confirmed using SDS-PAGE gel electrophoresis (Shapiro, A. L., et al., "Molecular Weight Estimation of Polypeptide Chains by Electrophoresis in SDS-Polyacrylamide Gels," *Biochem. Biophys. Res. Commun.* 28:815-820, 1967).

Figure 4:
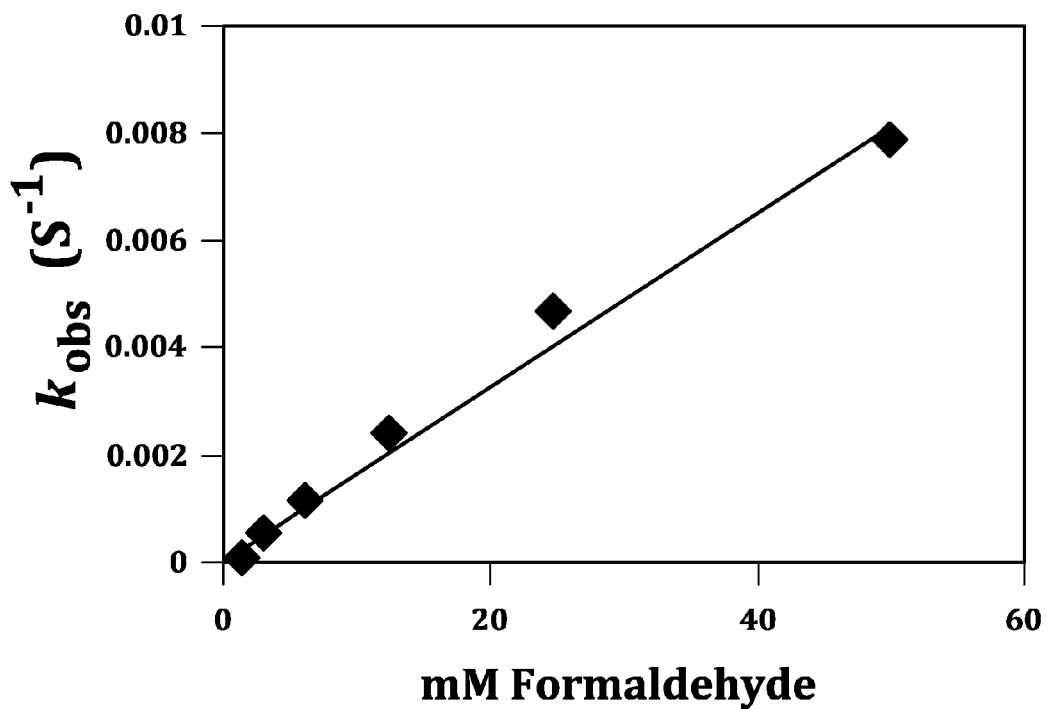
FIG. 4 illustrates the relationship between the initial concentration of formaldehyde and the observed rate of formaldehyde conversion to dihydroxyacetone by benzaldehyde lyase. The conversion rate of formaldehyde to dihydroxyacetone by benzaldehyde lyase was determined using a spectrophotometric-coupled assay that measures the oxidation of NADH by glycerol dehydrogenase during the subsequent (non-rate limiting) reduction of the dihydroxyacetone into glycerol, as described in Example 1.

Although the assay to monitor benzoin formation has been described (Janzen, E., et al., "Characterization of Benzaldehyde Lyase From *Pseudomonas Fluorescens*: a Versatile Enzyme for Asymmetric C—C Bond Formation," *Bioorganic Chem.* 34:345-361, 2006), there is no previously described assay for the real-time conversion of formaldehyde to dihydroxyacetone. Therefore, an assay was developed that coupled spectrophotometric measurements of NADH (Cook, P. F., and W. W. Cleland, *Enzyme Kinetics and Mechanism*, New York: Taylor & Francis Group; 2007) to the conversion of formaldehyde to dihydroxyacetone through BAL by the subsequent reduction of the dihydroxyacetone into glycerol through the oxidation of NADH by glycerol dehydrogenase (Janson, C. A., and W. W. Cleland, "The Kinetic Mechanism of Glycerokinase," *J. Biol. Chem.* 249:2562-2566, 1974), as described in Example 1. In order to validate that the rate-determining step being monitored in this assay is the reaction of BAL, both glycerol dehydrogenase and BAL concentration were varied independently to assess if the concentration of either enzyme was limiting to the velocity of the reaction. The rate of NADH oxidation was only dependent on the concentration of BAL, and was not dependent on concentration of glycerol dehydrogenase. As illustrated in FIG. 4, there is a clear dependence of reaction rate to formaldehyde substrate concentration, showing that BAL is capable of catalyzing the ligation of formaldehyde at approximately 0.02% of the catalytic efficiency that it ligates benzaldehyde. The activity of this enzyme for conversion of formaldehyde to dihydroxyacetone was further verified through the use of C13 NMR. Specifically, C13 NMR's were taken of dihydroxyacetone, C13 formaldehyde, BAL, and the combination of BAL and C13 formaldehyde. In the reaction, new peaks appeared that correspond to all three peaks observed in the dihydroxyacetone standard, strongly supporting that dihydroxyacetone is produced by BAL. This basal level of activity established the viability of BAL as a polypeptide scaffold for enzymatic catalysis of formaldehyde to dihydroxyacetone conversion.

B. Design and Production of Engineered Polypeptides Optimized to Convert Formaldehyde to Dihydroxyacetone Upon validation of BAL's activity for trimerizing formaldehyde into dihydroxyacetone, potential optimizing mutations to the enzyme active site were investigated to enhance the catalytic activity of the engineered enzyme to convert formaldehyde to dihydroxyacetone.

To date, there are two primary methods for engineering enzymes: "Directed Evolution" and "Rational Design" (Harris, J. L., and C. S. Craik, "Engineering Enzyme Specificity," *Curr. Opin. Chem. Biol.* 2:127-132, 1998). Directed Evolution is the process by which 1) a random library of enzyme variants is created (Stemmer, W. P. C., "Rapid Evolution of a Protein in vitro by DNA Shuffling," *Nature* 370:389-391, 1994; Kuchner, O., and F. H. Arnold, "Directed Evolution of Enzyme Catalysts," *Trends in Biotechnology* 15:523-530, 1997), 2) the enzyme with the greatest increase of the desired activity is identified either through a selection or screening assay and 3) the enzyme variant with the enhanced properties is isolated for further stepwise improvement. If the desired enzyme function can be made critical for an organism's survival, a selection assay for improved variants of an enzyme can generally be developed. This allows a large library of mutants to be screened (often approaching $10^{10}$), since the limiting step here is transformation efficiency. If the function is not critical for survival, a screening assay is necessary where the enzyme variant is individually tested for catalytic activity. The library size in this case is often dependent on the amount of time that needs to be spent on each variant. These libraries rarely get larger than $10^6$ variants due to these experimental restrictions. The major advantage of directed evolution is the minimal need for an understanding of either the protein structure or its mechanism. The major disadvantage of this method is that only small incremental changes are generally possible, due to the fact that most mutations lead to a loss in function, rather than gain in function (Arnold, F. H. "Design by Directed Evolution," *Accounts of Chemical Research* 31:125-131, 1998). This makes it necessary to perform many rounds of mutagenesis to identify promising "hits." Changes in activity using this monotonic optimization method are done in small, generally additive, steps (Yoshikuni, Y., and J. D. Keasling, "Pathway Engineering by Designed Divergent Evolution," *Curr. Opin. Chem. Biol.* 11:233-239, 2007) making it difficult to find a non-additive combinatorial set of mutations needed for drastic changes in activity. Still, a few combinatorial mutations have been reported (Seelig, B., and J. W. Szostak, "Selection and Evolution of Enzymes From a Partially Randomized Non-Catalytic Scaffold," *Nature* 448:828-831, 2007; Park, H.-S., et al. "Design and Evolution of New Catalytic Activity with an Existing Protein Scaffold," *Science* 311:535-538, 2006).

Rational Design is the process by which modifications to an enzyme are designed based on chemical principles and specific knowledge of the enzyme's structure and chemical mechanism. This method has been applied successfully in a growing number of cases (Yin, Y., and J. F. Kirsch, "Identification of Functional Paralog Shift Mutations: Conversion of *Escherichia coli* Malate Dehydrogenase to a Lactate Dehydrogenase," *Proc. Nat'l Acad. Sci. USA* 104:17353-17357, 2007; Rothman, S. C., and J. F. Kirsch "How Does an Enzyme Evolved In vitro Compare to Naturally Occurring Homologs Possessing the Targeted Function? Tyrosine Aminotransferase from Aspartate Aminotransferase," *J. Mol. Biol.* 327: 593-608, 2003; Yoshikuni, Y, et al. "Designed Divergent Evolution of Enzyme Function," *Nature* 440:1078-1082, 2006; Ballinger, M. D., et al. "A Variant of Subtilisin BPN' Engineered for Cleaving Tribasic Substrates," *Biochem.* 35:13579-13585, 1996; Chen, R., et al., "Redesigning Secondary Structure to Invert Coenzyme Specificity in Isopropylmalate Dehydrogenase," *Proc. Nat'l Acad. Sci. USA* 93:12171-12176, 1996; Hancock, S. M., et al. "Engineering of Glycosidases and Glycosyltransferases," *Curr. Opin. Chem. Biol.* 10:509-519, 2006). The major advantage of rational design is that one can introduce several mutations to an enzyme simultaneously such that the mutations are not mutually exclusive. Because so many mutations can be added at a time the number of proteins that need to be tested for activity is significantly smaller (generally less than $10^2$) than the number needed to be tested when using directed evolution (generally greater than $10^6$). The major disadvantage of rational design is the need for a deep understanding of the enzyme in question. Failure to properly account for all forces and interactions occurring within an active site can lead to misdirected optimization of the desired activity. Therefore rational design often relies on either a homologous protein, which can indicate structurally sound mutations that can be made to the enzyme, or a crystal structure in which the relative location of amino acids in the protein is known.

Another common approach is "Semi-Rational" design, which is the combined approach of directed evolution and rational design (Chica, R. A., et al., "Semi-Rational Approaches to Engineering Enzyme Activity: Combining the Benefits of Directed Evolution and Rational Design," *Curr. Opin. Biotech.* 16:378-384, 2005). In this case, a library of site-specific mutations, based on the knowledge of key areas in the enzyme to mutate, is made. In addition, the amino acids sampled at each site are usually restricted to the subset that is hypothesized to most likely enhance the desired properties of the enzyme. The library sizes of enzyme variants generated using the semi-rational approach is generally between $10^2$ and $10^6$.

Recently the idea of computational enzyme design has emerged in program suites such as ROSETTA (Ashworth, J., et al. "Computational Redesign of Endonuclease DNA Binding and Cleavage Specificity," *Nature* 441:656-659, 2006; Rothlisberger, D., et al., "Kemp Elimination Catalysts by Computational Enzyme Design," *Nature* 453:190-U194, 2008; Korkegian, A., et al. "Computational Thermostabilization of an Enzyme," *Science* 308:857-860, 2005; Zanghellini, A., et al., "New Algorithms and an in Silico Benchmark for Computational Enzyme Design," *Protein Sci.* 15:2785-2794, 2006; Jiang, L., et al., "De novo Computational Design of Retro-Aldol Enzymes," *Science* 319:1387-1391, 2008), DEZYMER (Pinto, A. L., et al., "Construction of a Catalytically Active Iron Superoxide Dismutase by Rational Protein Design," *Proc. Nat'l Acad. Sci. USA* 94:5562-5567, 1997), and ORBIT (Bolon, D. N., and S. L. Mayo, "Enzyme-Like Proteins by Computational Design," *Proc. Nat'l Acad. Sci. USA* 98:14274-14279, 2001). While each program suite is significantly different, they all provide a way around many of the traditional problems faced by Direction Evolution or Rational Design. The general strategy of computational enzyme design is to use a force field composed of 1) empirically derived potentials (Lennard-Jones 6-12 (Lennard-Jones, J. E., "Cohesion," *Proc. Physical Soc.* 1931:461), orientation dependent hydrogen bonding (Kortemme, T., and D. Baker, "A Simple Physical Model for Binding Energy Hot Spots in Protein-Protein Complexes," *Proc. Nat'l Acad. Sci. USA* 99:14116-14121, 2002), Coulomb electrostatics, and implicit solvation (Lazaridis, T., and M. Karplus, "Effective Energy Function for Proteins in Solution," *Proteins: Structure, Function, and Genetics* 35:133-152, 1999)) and 2) statistically derived potentials (Ramachandran angles (Ramachandran, G. N., et al., "Stereochemistry of Polypeptide Chain Configurations," *J. Mol. Biol.* 7:95-99, 1963), side chain torsions (Dunbrack, R. L., Jr., and F. E. Cohen, "Bayesian Statistical Analysis of Protein Side-Chain Rotamer Preferences," *Protein Sci.* 6:1661-1681, 1997), pair potentials (Simons, K. T., et al., "Improved Recognition of Native-Like Protein Structures Using a Combination of Sequence-Dependent and Sequence-Independent Features of Proteins," *Proteins* 34:82-95, 1999), etc.) to evaluate how mutations in the protein effect the energetics of both the interactions with the protein to itself and with protein to the transition state of the desired reaction. The programs search heuristically through all of the possible combinations of mutations, evaluating the energetics for each set of mutations, and return the set of mutations determined to be most favorable for interacting with the transition state. This allows for combinatorial mutations to be found while assessing the physical interaction between the protein with itself and the protein with the transition state for each set of mutations.

The ROSETTA program suite was used to computationally design enzyme modifications to the BAL scaffold to enhance both its efficiency and specificity towards the formaldehyde to dihydroxyacetone reaction. The computational design procedure using the ROSETTA software suite has been previously described (Ashworth, J., et al. "Computational Redesign of Endonuclease DNA Binding and Cleavage Specificity," *Nature* 441:656-659, 2006; Rothlisberger, D., et al., "Kemp Elimination Catalysts by Computational Enzyme Design," *Nature* 453:190-U194, 2008; Korkegian, A., et al. "Computational Thermostabilization of an Enzyme," *Science* 308:857-860, 2005; Jiang, L., et al., "De novo Computational Design of Retro-Aldol Enzymes," *Science* 319:1387-1391, 2008). As no direct addition was made to this approach, only a high-level description of how the three algorithms (ROSETTA, ROSETTALIGAND, and ROSETTADESIGN) are used for the design of enzymes in silico is provided. Briefly, ROSETTA uses an energy function based on a semi-empirical force field (as discussed previously) to optimize the relative geometric conformations of the amino acids using a Monte Carlo simulated annealing protocol (Rohl, C. A., et al., "Protein Structure Prediction Using Rosetta," *Meth. Enzymol.* 383:66-93, 2004). ROSETTADESIGN includes the ability to change the identity, as well as the conformation of the protein's amino acids (Kuhlman, B., and D. Baker, "Native Protein Sequences Are Close to Optimal for Their Structures," *Proc. Nat'l Acad. Sci. USA* 97:10383-10388, 2000; Kuhlman, B., and D. Baker, "Exploring Folding Free Energy Landscapes Using Computational Protein Design," *Curr. Opin. Structural Biol.* 14:89-95, 2004). ROSETTALIGAND adds the ability to evaluate a protein-ligand intermolecular interface in addition to the protein-protein intramolecular interface (Meiler, J., and D. Baker, "ROSETTALIGAND: Protein-Small Molecule Docking With Full Side-Chain Flexibility," *Proteins: Structure, Function, and Bioinformatics* 65:538-548, 2006). The present combined use of the program suite of ROSETTA, ROSETTADESIGN, and ROSETTALIGAND allows the effective design of enzymes capable of interacting with new ligands. It is important to note that as proposed by Pauling (Pauling, L., "Molecular Architecture and Biological Reactions," *Chemical & Engineering News* 24:1375-1377, 1946; Pauling, L., "Nature of Forces Between Large Molecules of Biological Interest," *Nature* 161:707-709, 1948), and advanced by Wolfenden (Wolfenden, R., "Analog Approaches to the Structure of the Transition State in Enzyme Reactions," *Acc. Chem. Res.* 5:10-18, 1972), it has been theorized that an enzyme's proficiency is proportional to its affinity towards the transition state (TS) of the reaction. Therefore, when working with ROSETTA to optimize ligand-protein interactions, the design approach focused on the optimization of the protein interaction with the TS more than the substrate or product.

The first step of the enzyme engineering process required the construction of a model of the TS. To do this the 3D modeling program Spartan (Wavefunction: Spartan 3D Student Edition. Edited by: Wavefunction Inc.) was used to add dihydroxyacetone adjacent to the thiamine diphosphate (ThDP) cofactor. The original three-dimensional structure of ThDP was obtained from the known crystal structures of Benzaldehyde lyase (PDB ID: 2AG0 or 3D7K). The orientation of dihydroxyacetone relative to the ThDP cofactor was optimized in the presence of the catalytic histidine and glutamine of the BAL active site motif. The optimal orientation was based on previously documented models of substrate analogues built into the active site (Brandt, G. S., et al., "Probing the Active Center of Benzaldehyde Lyase with Substitutions and the Pseudosubstrate Analogue Benzoylphosphonic Acid Methyl Ester," *Biochem.* 47:7734-7743, 2008). The three dimensional model of the transition state and protein structure was input into the ROSETTA program, in addition to a list of amino acids in the active site to design, minimize or remain fixed (such as catalytic residues) based on chemical principles. Finally, geometric constraints for how the transition state should interact with the catalytic residues of the protein were included such that hydrogen bonds as described between the Histidine-29, Glutamate-50, and Glutamine 113 (of SEQ ID NO:2) would remain fixed in space and not significantly change during the computational simulations. The ROSETTA algorithm was then allowed to run and three-dimensional models of the redesigned protein were output. The resulting output model (and corresponding amino acid sequence) was the ROSETTA-predicted optimal enzyme for interacting with the formaldehyde to dihydroxyacetone transition state.

In addition, an alternative approach to the standard design method was investigated. The standard design method was modified by allowing only a subset of the 20 amino acids in each position in the active site. This directed search was based on knowledge of chemical stabilization energetics, allowing ROSETTA to only sample amino acid subsets based on 1) homologous protein structures and 2) the assumption that "holes" created by removing the phenyl groups from benzaldehyde would need to be hydrophobically filled in. From these two assumptions the search of potential active sites was narrowed from $10^{10}$ to $10^6$. While experimentally testing either of these sets of combinations is impractical with traditional laboratory methods, ROSETTA was able to screen through both the full design set (all 20 amino acids at each position) and the directed design set (homolog and hole filling amino acids) in less than a day.

Figure 6:
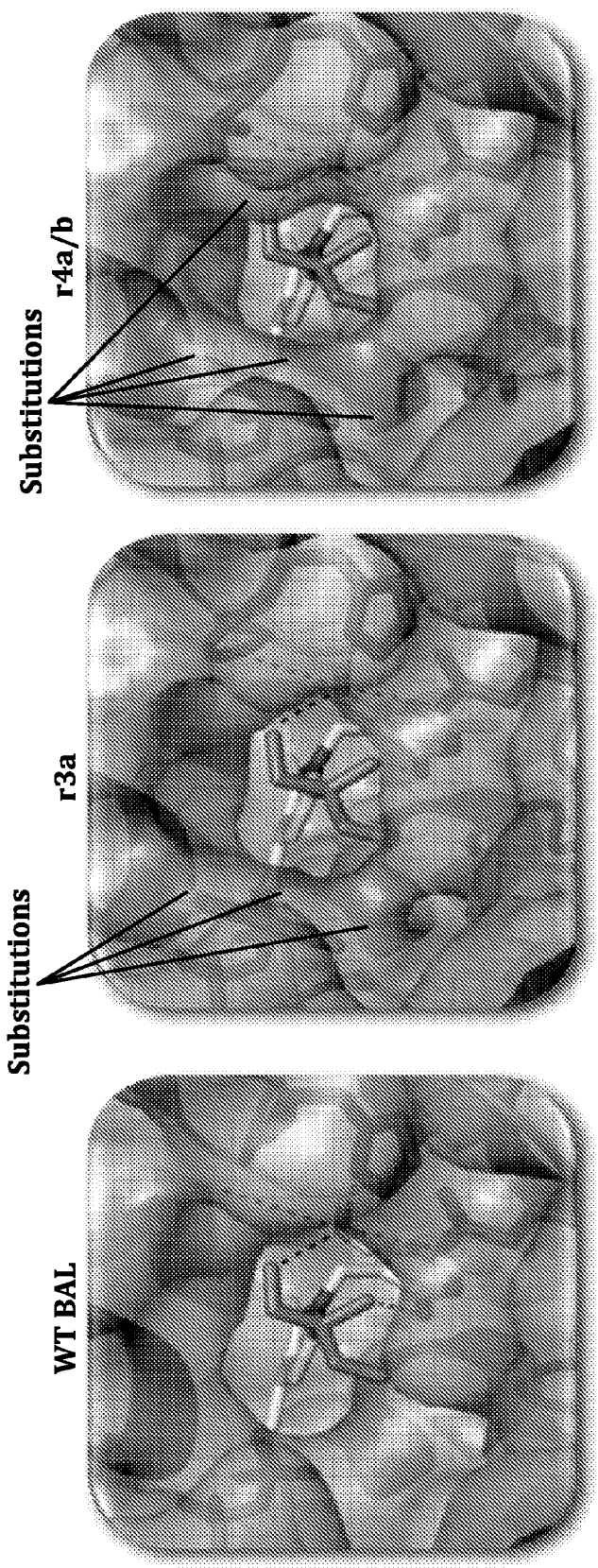
FIGS. 6A-6C illustrate the computational models of active sites of benzaldehyde lyase (BAL) (FIG. 6A), and the engineered formolase r3a (FIG. 6B) and engineered formolase r4a/b (FIG. 6C) enzymes. For each enzyme, the protein is displayed in surface view to aid in the visualization of the shape complementarity towards the new substrate/product. The amino acid substitutions incorporated in the formolase r3a and formolase r4a engineered polypeptides are indicated, and shown beneath the surface view in sticks. In formolase r3a, the A28S, A394G, and A480W substitutions fill in space above the transition state. In formolase r4a, the same three r3a mutations are retained, in addition to the added G319N mutation that provide an additional hydrogen bond to the hydroxyl groups of the new product.

When using the standard design methodology, ROSETTA predicted that the triple mutant containing the mutations A28S, A394G, and A480W, referred to herein as formolase r3a, is optimal for the input TS. The amino acid sequence for formolase r3a is set forth herein as SEQ ID NO:4. The three amino acid substitutions at these positions fill the cavity behind the TS that had been occupied by the phenyl groups of benzoin, the typical product catalyzed by wild type BAL. For the directed design, ROSETTA predicted that four mutations in the BAL sequence would be optimal for the input TS: A394G, A480W, A28S and G419N. This engineered enzyme is referred to as formolase r4a, and the amino acid sequence is set forth herein as SEQ ID NO:8. Three of the mutations are identical to the mutations predicted for formolase r3 (i.e., A28S, A394G and A480W), but an additional substitution G419N were predicted to introduce additional hydrogen bonds to the hydroxyls of the dihydroxyacetone TS. The G419N mutation introduces a new hydrogen bond to the hydroxyl group which is only present in the dihydroxyacetone TS. The dihydroxyacetone TS within BAL, and two illustrative top scoring designs from these ROSETTA simulations (referred to herein as "formolase" r3a and r4a) in FIGS. 6A-6C. In the views of the three enzymes, the protein is displayed in surface view to aid in the visualization of the improved shape complementarity towards the new substrate. The mutations from the wild type BAL scaffold sequence are indicated, and are shown beneath the surface view in sticks.

In order to generate the enzyme variants to test these designs, the Kunkel mutagenesis method (Kunkel, T. A., "Rapid and Efficient Site-Specific Mutagenesis Without Phenotypic Selection," *Proc. Nat'l Acad. Sci. USA* 82:488-492, 1985) was employed to generate the triple mutant from the full design (formolase r3a) and the quadruple mutant from the directed design (formolase r4a). Furthermore, additional formolase variations utilizing different combinations of the ROSETTA-suggested substitutions described supra were generated. Specifically, triple mutant formolase r3b was generated with the substitutions G419N, A394G, and A480W in the wild time BAL sequence, having an amino acid sequence set forth herein as SEQ ID NO:5. Triple mutant formolase r3c was generated with the substitutions A28S, G419N, and A480W in the wild time BAL sequence, having an amino acid sequence set forth herein as SEQ ID NO:6. Triple mutant formolase r3d was generated with the substitutions A28S, G419N, and A394G in the wild time BAL sequence, having an amino acid sequence set forth herein as SEQ ID NO:7. Finally, an alternative four-mutant formolase, formolase r4b, was generated. Formolase r4b, has the same substitutions as r4a, with the exception of an A28I substitution instead of an A28S substitution. The A28I substitution was predicted to increase the number of molecular interactions between the transition state and the engineered protein over the wild type sequence. The amino acid sequence of formolase r4b is set forth herein as SEQ ID NO:9. A description of the technique used to create the described formolase variations is provided in Example 2.

Upon verification of the mutagenesis through DNA sequencing, the protein products were expressed, purified, and assayed for activity with formaldehyde substrate, according to the method described in Example 3. For comparison, in some instances the activities of the enzymes were also assayed for the benzaldehyde, the typical substrate for BAL. The results are shown in TABLE 1. As predicted by ROSETTA, the r3a and r4 mutants showed an increased activity towards formaldehyde. Various additional three-mutant formolases (r3b-r3d) and an alternative four-mutant formolase also exhibited increased activity toward formaldehyde. The four-mutant formolases, namely r4a and r4b, were most active towards formaldehyde. Comparative analysis indicated that the formolase r4a was also least active towards benzaldehyde, the typical BAL substrate. In this regard, the formolase r4a enzyme exhibited an overall 34,000-fold switch in specificity and was shown to be more active towards the desired formaldehyde substrate than the benzaldehyde substrate.

TABLE 1

Comparison of the activity and specificity of wild type BA, r3, and r4 formolase engineered polypeptides using the BAL scaffold

|  | BAL | r3a | r3b | r3c | r3d | r4a | r4b |
|---|---|---|---|---|---|---|---|
| SEQ ID NO: | 2 | 4 | 5 | 6 | 7 | 8 | 9 |
| Formaldehyde $k_{cat}/K_M$ (M$^{-1}$ s$^{-1}$) | 0.16 | 0.94 | 1.5 | 0.3 | 0.1 | 1.78 | 3.6 |
| Benzaldehyde $k_{cat}/K_M$ (M$^{-1}$ s$^{-1}$) | 831.0 | 47.6 | N/A | N/A | N/A | 0.26 | N/A |
| Relative Substrate Preference Towards Formaldehyde: Catalytic Efficiency on Formaldeyde/Benzaldehyde | $1.95 \times 10^{-4}$ | $1.97 \times 10^{-2}$ | N/A | N/A | N/A | 6.72 | N/A |
| Specificity Switch Towards Formaldehyde: Substrate Preference Towards Formaldehyde of Formolase Variant/BAL | 1 | 101 | N/A | N/A | N/A | 34,461 | N/A |

Additional substitution mutations were predicted to moderately enhance the activity of formolase r4b to convert formaldehyde to dihydroxyacetone. Many of these mutations were incorporated into the formolase r4b enzyme and the resulting enzymes were assayed for activity, according to the procedure described supra. However, these mutations did not result in any significant increase in activity over the formolase r4b background. TABLE 2 lists these additional substitutions, with reference to the amino acid positions corresponding to the BAL sequence (SEQ ID NO:2). Thus, the mutations listed in TABLE 2 provide guidance for tolerable variation within the scaffold and/or motif sequence.

TABLE 2

Additional mutations incorporated into formolase r4b that did not significantly enhance the catalytic activity to convert formaldehyde into dihydroxyacetone. The number refers to the amino acid residue position with reference to the original sequence of BAL, set forth in SEQ ID NO: 2. Each line represents a distinct candidate formolase enzyme that was tested.

| Original Amino Acid | Residue Position | New Amino Acid |
|---|---|---|
| L | 25 | F |
| L | 25 | R |
| M | 421 | I |
| M | 421 | Q |
| M | 421 | F |
| M | 421 | L |
| M | 421 | E |
| L | 112 | Y |
| L | 112 | M |
| L | 112 | K |
| L | 112 | R |
| L | 112 | F |
| G | 27 | A |
| G | 27 | S |
| G | 27 | T |
| L | 282 | R |
| L | 282 | M |
| L | 282 | F |
| L | 282 | Y |
| L | 282 | W |
| L | 282 | K |
| N | 419 | Q |
| N | 419 | E |
| N | 419 | D |
| N | 419 | K |
| N | 419 | R |
| Y | 397 | M |
| Y | 397 | L |
| Y | 397 | K |
| F | 484 | W |

TABLE 2-continued

Additional mutations incorporated into formolase r4b that did not significantly enhance the catalytic activity to convert formaldehyde into dihydroxyacetone. The number refers to the amino acid residue position with reference to the original sequence of BAL, set forth in SEQ ID NO: 2. Each line represents a distinct candidate formolase enzyme that was tested.

| Original Amino Acid | Residue Position | New Amino Acid |
|---|---|---|
| F | 484 | L |
| F | 484 | I |
| F | 484 | V |
| F | 484 | R |
| F | 484 | K |
| Q | 113 | E |
| Q | 113 | M |
| Q | 113 | L |
| H | 29 | D |
| W | 163 | K |
| W | 163 | R |
| W | 480 | Y |
| W | 480 | R |
| W | 480 | K |
| I | 15 | K |
| IK | 15-16 | RE |
| T | 32 | A |
| P | 43 | R |
| G | 64 | T |
| A | 65 | G |
| GA | 64-65 | TG |
| G | 76 | P |
| P | 84 | G |
| G | 102 | P |
| A | 103 | P |
| GA | 102-103 | PP |
| M | 133 | T |
| H | 137 | R |
| A | 152 | G |
| APR | 152-154 | GRP |
| A | 187 | P |
| AR | 187-188 | PG |
| A | 199 | E |
| E | 214 | G |
| Y | 261 | A |
| H | 286 | G |
| H | 286 | Y |
| HG | 286-287 | GR |
| C | 306 | A |
| Q | 312 | R |
| QGIA | 312-314 | RPID |
| LTY | 395-397 | EAA |
| T | 427 | F |
| A | 438 | P |
| DLEAG | 435-439 | (—)APD |
| T | 442 | V |

TABLE 2-continued

Additional mutations incorporated into formolase r4b that did not significantly enhance the catalytic activity to convert formaldehyde into dihydroxyacetone. The number refers to the amino acid residue position with reference to the original sequence of BAL, set forth in SEQ ID NO: 2. Each line represents a distinct candidate formolase enzyme that was tested.

| Original Amino Acid | Residue Position | New Amino Acid |
|---|---|---|
| S | 454 | H |
| K | 464 | H |
| F | 484 | G |
| V | 489 | Y |
| A | 513 | G |
| A | 526 | P |
| Q | 530 | R |
| HN | 534-535 | SG |
| A | 545 | D |
| P | 550 | H |
| E | 553 | T |
| L | 112 | D |
| L | 112 | E |
| L | 112 | N |
| L | 112 | R |
| L | 112 | K |
| I | 28 | K |
| I | 28 | D |
| I | 28 | R |
| I | 28 | G |
| F | 484 | Y |
| W | 163 | R |
| N | 419 | E |
| Y | 397 | R |
| W | 480 | R |

In addition to the use of BAL as a formolase scaffold, described supra and identified by SEQ ID NO:2, a BAL homolog was similarly tested for potential as a formolase scaffold. Specifically, the BAL homolog, accession number NP_945464.1, with an amino acid sequence set forth herein as SEQ ID NO:3, was expressed in wild type form and a "Design" form that incorporated the four mutations corresponding to the mutations introduced into formolase r4a. The expressed proteins were tested for activity as described above and in Example 1. The wild type form of the BAL homolog had an observed 2 fold increase activity toward formaldehyde over background. Considering that BAL homolog 20 has approximately 40% sequence identity with wild type BAL, it appears that considerable sequence variation is tolerated in a formolase scaffold polypeptide. However, incorporation of the substitutions that enhanced the formolase r4a enzyme in the corresponding residue positions in the BAL homolog (SEQ ID NO:3) decreased the basal level of activity. Therefore, it is apparent that the results ROSETTA modeling for one BAL homolog is not likely transferable across the family of BAL homolog protein. Instead, use of any of BAL homologs as formolase scaffolds will require individual modeling analysis for each candidate homolog to generate a functional active site motif.

C. Incorporation of the Formolase Enzymes into a Pathway to Convert Carbon Dioxide to C3 Compounds Computational modeling enabled the production of engineered enzymes that that catalyze the conversion of the C1 metabolite formaldehyde into the C3 metabolite dihydroxyacetone. In the case of engineered formolase, r4a exhibited approximately a 34,000-fold switch in substrate preference (TABLE 1). Upon creation of various engineered formolase enzymes (also referred to as FLS) the creation of the carbon dioxide fixation pathway in vitro was pursued to establish and assess the viability of a formolase as a pathway component in the generation of C3 compounds from carbon dioxide precursors. C3 compounds, such as dihydroxyacetone, can then be converted through known glycolysis pathways into acetyl-CoA as the starting point for synthesis of commodity molecules.

An initial target is the production of investigation was the production of formate to act as a substrate for the engineered formolase enzymes. To build a successful pathway to convert formate into formaldehyde, the present investigation focused on two enzymes, acetyl-CoA synthase (ACS), which is ATP and CoA dependent, and acylating acetaldehyde dehydrogenase (ADH), which is NADH and CoA dependent. Both of these enzymes exist are known in *E. coli*, have been previously cloned and characterized, and are reported as reversible (Lin, H., et al., "Acetyl-CoA Synthetase Overexpression in *Escherichia coli* Demonstrates More Efficient Acetate Assimilation and Lower Acetate Accumulation: a Potential Tool in Metabolic Engineering," *Appl. Microbiol. and Biotech.* 71:870-874, 2006; Kumari, S., et al., "Cloning, Characterization, and Functional Expression of ACS, the Gene Which Encodes Acetyl-Coenzyme-A Synthetase in *Escherichia-Coli,*" *J. Bacteriol.* 177:2878-2886, 1995; Lee, S.-J., et al., "Coupled Expression of MhpE Aldolase and MhpF Dehydrogenase in *Escherichia coli,*" *Biochem. and Biophys. Res. Commun.* 346:1009-1015, 2006; Yan, R. T., and J. S. Chen, "Coenzyme A-Acylating Aldehyde Dehydrogenase from *Clostridium-Beijerinckii* Nrrl-B592," *Applied and Environmental Microbiology* 56:2591-2599, 1990). These two enzymes are typically known to act in concert to convert acetate to acetaldehyde. However, these enzymes have not been explicitly tested for activity with formate in the direction of interest to produce formaldehyde, a schematic illustration of which is provided in FIG. 1. In order to test this potential pathway both genes were cloned from *E. coli* MG1655. Briefly, primers annealing to the 5' and 3' ends of the genes and introducing flanking restriction sites were used to amplify the genes from *E. coli*. The amplicons were inserted into the pET29b+ expression vector using standard cloning techniques. The polypeptides for the ACS and ADH, with the amino acid sequence set forth in SEQ ID NOS:10 and 11, respectively, were expressed and purified as previously described. The sequences reflect incorporated HIS tags used to facilitate purification. As with BAL, both enzymes expressed very strongly and resulted in clean preparations from the IMAC purification.

Figure 7:
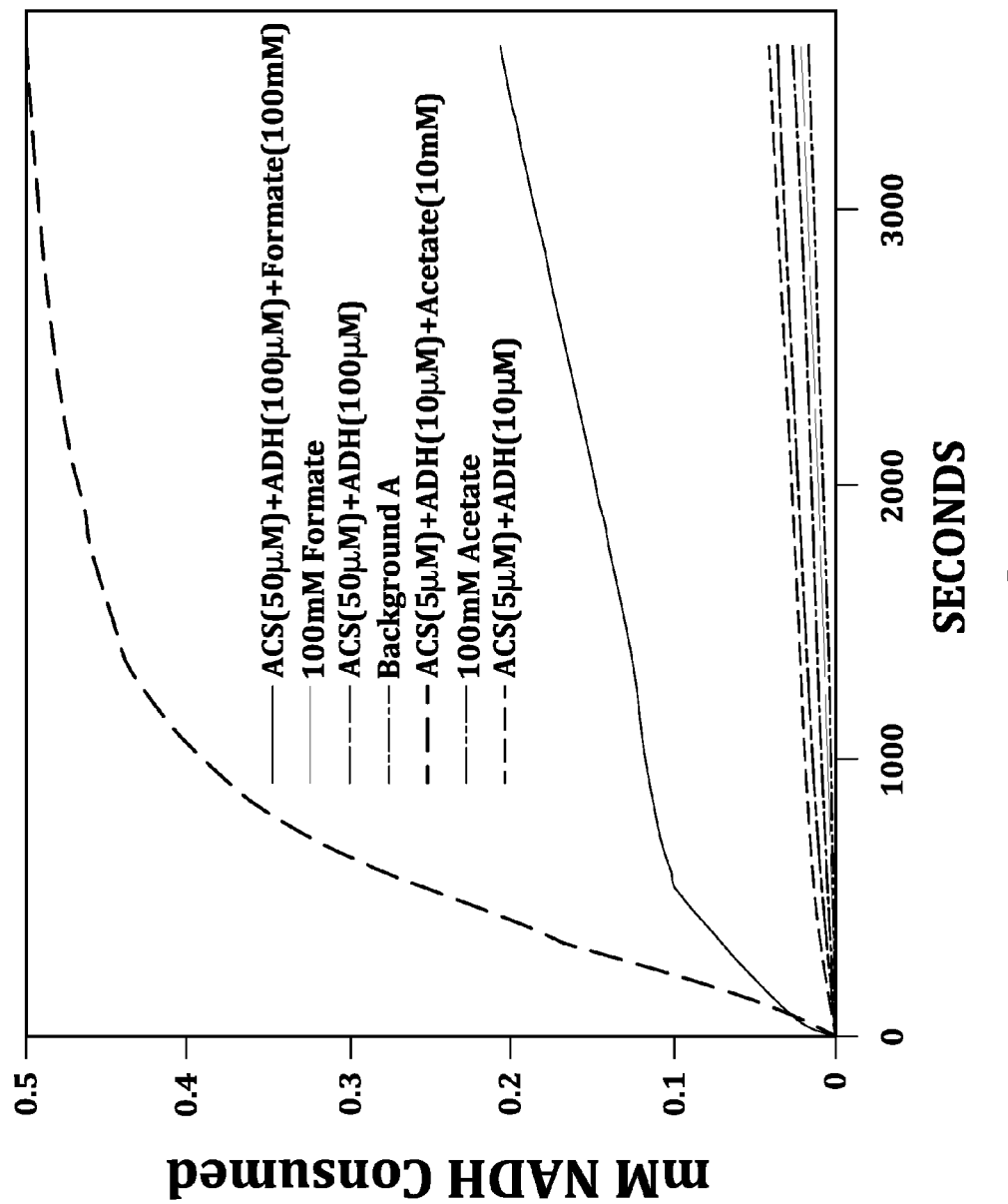
FIG. 7 graphically illustrates the NADH consumption over time assayed in reactions containing the indicated concentrations of ACS, ADH, formate and/or acetate, which indicate the relative activity of ACS and ADH to form aldehyde products from the acid substrates, as described in Example 4.

The purified ACS and ADH enzymes were assayed for activity in the conversion of formate to formaldehyde, as described in Example 4. The reaction conditions selected were a hybrid of what had been previously reported for the two enzymes. The ACS enzyme converts the acid and (HS)-CoA into the acyl-CoA in an ATP-dependent reaction. The ADH enzyme reduces the acyl-CoA to the thioester in an NADH-dependent reaction. Therefore the NADH-dependent conversion of the acid to aldehyde was monitored by the consumption of NADH. The activities of the ACS and ADH enzymes with acetate or formate as substrates were compared with varying reaction parameters. As illustrated in FIG. 7, the ACS/ADH pathway is capable of converting formate to formaldehyde, even though the pathway is approximately two hundred-fold more efficient with the typical acetate substrate than with formate substrate. Interestingly, the formate progress curve indicates that formic acid and formaldehyde come to equilibrium rather quickly, unlike acetate and acetaldehyde, which do not appear to reach an observable equilibrium under the experimental conditions used. Additional control reactions demonstrated the need for both ACS and ADH.

In this regard, if either ACS or ADH were absent from the solution, no NADH consumption above background was observed.

Figure 2:
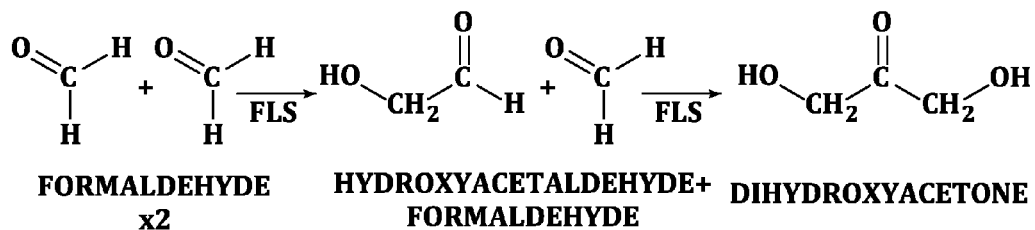
FIG. 2 schematically illustrates the conversion of formaldehyde to dihydroxyacetone by an engineered formolase (FLS) enzyme in a two-step process.
Figure 8:
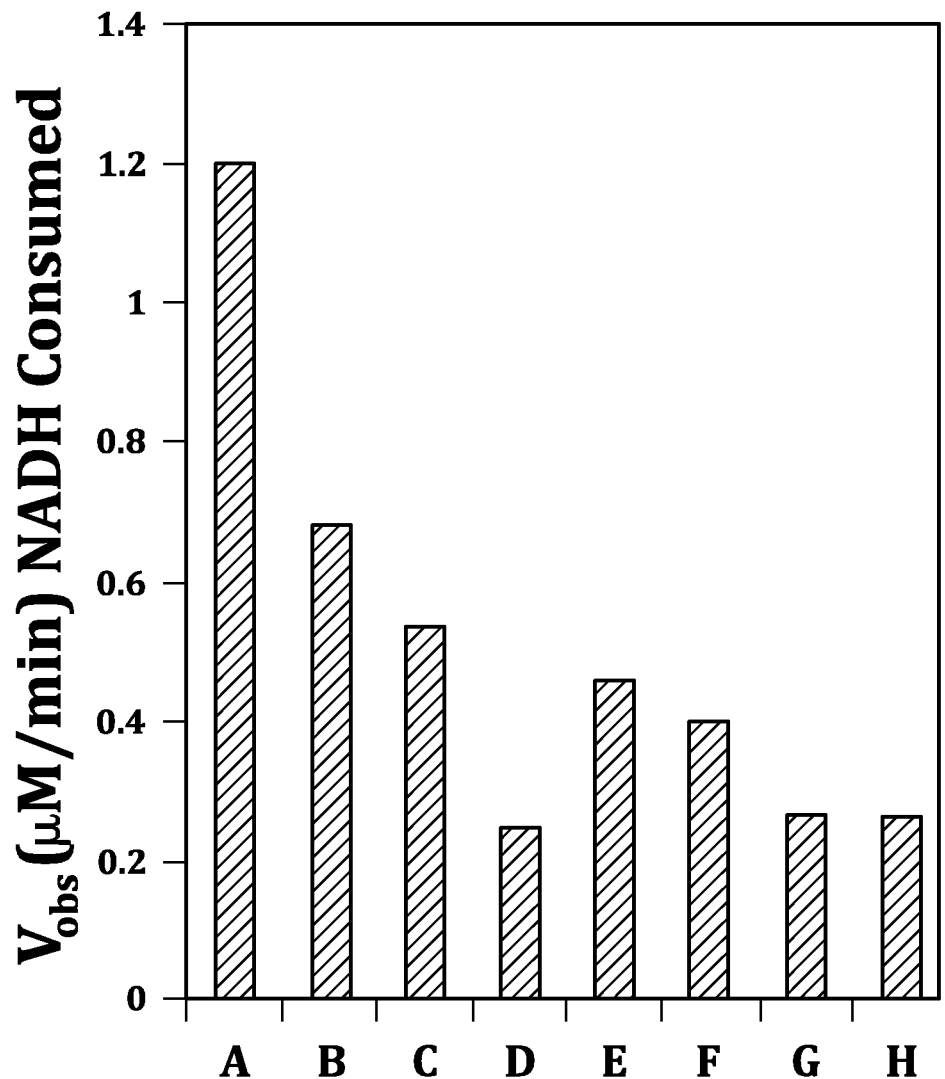
FIG. 8 graphically illustrates the observed rate of formolase-dependent NADH consumption in several reactions combining ACS, ADH, and formolase, with or without formate. The formolase-dependent NADH consumption was determined using the spectrophotometric-coupled assay measuring the oxidation of NADH by glycerol dehydrogenase during the subsequent reduction of the dihydroxyacetone into glycerol. The reactions incorporate the 50 μM ACS+100 μM ADH, under the same reaction conditions used for the reaction illustrated in FIG. 7, in addition to varying concentrations of formolase (FLS) variant r4b with or without formate. Specifically, the bars refer to the following reaction variations: A) 100 μM FLS+100 mM formate; B) 50 μM FLS+100 mM formate; C) 25 μM FLS+100 mM formate; D) 0 μM FLS; E) 100 μM FLS; F) 50 μM FLS; G) 25 μM FLS; H) 0 μM FLS, as described in Example 5.

Considering the successful use of ACS and ADH to convert formate to formaldehyde, as depicted in FIG. 1, and the independent use of engineered formolase enzymes to convert formaldehyde to dihydroxyacetone, as depicted in FIG. 2, the compatibility of the conversion pathways within a single reaction cascade was investigated. An illustration of the entire reaction is schematically depicted in FIG. 3. Specifically, reactions incorporating ACS, ADH, and formolase r4b were run with varying concentrations of the formolase enzyme and initial starting substrate (formate), as described in Example 5. The conversion rate of formaldehyde to dihydroxyglycerol dehydrogenase was assayed by further allowing the NADH-dependent reduction of the dihydroxyacetone to glycerol by glycerol dehydrogenase, as described supra and in Example 3. As illustrated in FIG. 8, the rate of NADH consumption is directly related to the starting concentration of the formolase enzyme. This is a strong indication that the pathway is functional, and currently formaldehyde accrues until it reaches equilibrium. At that point formolase becomes the rate-limiting agent. Therefore, additional variants of formolase with improved catalytic efficiency are predicted to increase the throughput of the reaction, such that formolase has sufficient catalytic parity with the rest of the enzymes in the pathway for the continuous flow of the starting C1 compound substrate into central metabolism.

The following examples are provided for the purpose of illustrating, not limiting, the invention.

EXAMPLES

Example 1

The Spectrophotometric Assay to Determine BAL Activity to Convert Formaldehyde to Dihydroxyacetone In this example, an enzyme-coupled spectrophotometric assay to determine the velocity of BAL to convert formaldehyde to dihydroxyacetone is described.

To assess the activity of BAL to convert formaldehyde to dihydroxyacetone, the reaction was coupled to an additional reaction wherein dihydroxyacetone is further reduced to glycerol through the oxidation of NADH by glycerol dehydrogenase and the consumption of NADH is monitored spectrophotometrically at 340 nm. The change in absorbance at 340 nm resulted from the oxidation-reduction reaction of NADH to NAD and dihydroxyacetone to glycerol catalyzed by the coupling enzyme glycerol dehydrogenase. The starting concentrations of BAL and glycerol dehydrogenase were varied independently to ensure that the concentration of glycerol dehydrogenase was not a limiting factor to the reaction, and therefore the rate of NADH consumption was reflective of the velocity of BAL to convert formaldehyde to dihydroxyacetone.

The representative assay reflecting BAL activity was performed in potassium phosphate buffer, pH 8, at room temperature (25° C.). The reaction contained 2 mM MgSO4, 0.2 mM ThDP, 40 µM BAL, 0.1 mg/ml glycerol dehydrogenase, and 0.5 mM NADH. Starting concentrations of formaldehyde substrate ranged from 0 to 50 mM (0, 2, 4, 6, 12, 25 and 50 mM). The steady state portion from each formaldehyde concentration progress curve was used to generate the observed rates, as illustrated in FIG. 4. Because no significant saturation appears to occur over the substrate range assayed, the $k_{cat}/K_M$ can be determined based only on the initial linear portion of the curve.

Example 2

Generation of Engineered Formolase Enzymes Based on the BAL Scaffold Sequence

This example describes the generation of the amino acid residue substitutions A394G, A480W, G419N, A28S, and A28I, which in various combinations result in the r3 and r4 formolase variants.

The Kunkel mutagenesis applied to generate each mutant was described by Kunkel, T. A. (1985) Proc Natl Acad Sci USA 82, 488-492. Briefly, single stranded dU-DNA was generated and a primer encoding the desired mutation with flanking regions to specifically anneal to the targeted site on SEQ ID NO:1. Annealing was performed by heating the reaction to 98° C. melting temperature, and then allowing the reaction to cool to room temperature over the course of an hour. After annealing the DNA was elongated using T4 polymerase according to manufacturer's instructions. Next, the extended DNA products were ligated together in the various combinations corresponding to the r3 and r4 mutants using and NEB T4 ligase according to manufacturer's instructions. The final mutated gene templates were inserted into an expression vector and transformed into BL21(DE3) cells. All polypeptides were expressed with HIS tags to facilitate purification. Single colonies were sequenced to verify the desired mutation had been incorporated.

Example 3

The Spectrophotometric Assay to Compare the Activities of BAL and the Formolase Variants to Convert Formaldehyde to Dihydroxyacetone In this example, the application of the enzyme-coupled spectrophotometric assay, described in Example 1, to determine the velocity of BAL and the engineered formolase enzyme variants to convert formaldehyde to dihydroxyaceton is described.

Measurements of conversion rate of formaldehyde to dihydroxyacetone were performed through the enzyme-coupled spectrophotometric assay described in Example 1, wherein the NADH consumption resulting from the reduction of dihydroxyacetone to glycerol is measured. Individual reactions contained 5 µM of the enzyme (BAL, FLS r3a, FLS r3b, FLS r3c, FLS r3d, FLS r4a, and FLS r4b), 0.1 mg/mL glycerol dehydrogenase, 1 mM NADH, 50 mM potassium phosphate buffer at pH 8.0, 0.2 mM thiamine diphosphate 2 mM MgSO4, and formaldehyde ranging from 0 to 50 mM. The change in absorbance at 340 nm was monitored, which resulted from the oxidation-reduction reaction of NADH to NAD and dihydroxyacetone to glycerol catalyzed by the coupling enzyme glycerol dehydrogenase. An increased rate of dihydroxyacetone production from formaldehyde by formolase enzymes resulted in an increased rate of NADH oxida-

Example 4

The Spectrophotometric Assay to Determine the Combined Activities of ACS and ADH to Convert Formate to Formaldehyde In this example, the assay used to determine the activity of ACS and ADH to convert formate to formaldehyde is described.

The ability of ACS to catalyze the ATP-dependent attachment CoA to formate to form formyl-CoA, and the subsequent reduction of formyl-CoA to the aldehyde form (i.e., formaldehyde) by ADH in a NADH-dependent manner, was tested. See FIG. 1 for an illustrative scheme of the reaction. Reactions testing the activities of ACS and ADH in this hypothesized conversion were run at room temperature in 50 mM potassium phosphate, with 0.5 mM NADH, 300 mM KCl, 1 mM DTT, 0.2 mM ThDP, 0.2 mM CoA, 2 mM $MgSO_4$. The starting formate concentration was either 0 or 100 mM. Enzyme concentrations were varied in several combinations. ACS concentrations were 0, 5 or 50 μM. ADH concentrations were 0, 10 or 100 μM. As a control, some reactions used 10 or 100 mM of acetate as the starting substrate, which is the typical substrate for ACS. NADH consumption resulting from the reduction of formyl-CoA in the second step of the reaction was monitored spectrophotometrically at 340 nm and converted to a concentration value using the extinction coefficient of 6620 $M^{-1}$ $cm^{-1}$. The results are illustrated in FIG. 7. Additional controls demonstrated the need for both ACS and ADH. In this regard, if either ACS or ADH were absent from the solution, no NADH consumption above background was observed.

Example 5

The Spectrophotometric Assay to Determine the Combined Activities of ACS, ADH and FLS to Convert Formate to Dihydroxyacetone in a Single Reaction Cascade In this example, the assay used to determine the combined activity of ACS, ADH and FLS to convert formate to dihydroxyacetone is described.

A general assay was run to test the combined activity of ACS, ADH and FLS to convert formate to dihydroxyacetone. The assay combined the approaches described in Examples 1 and 4. Reactions were carried out at room temperature in 50 mM potassium phosphate, with 0.5 mM NADH, 300 mM KCl, 1 mM DTT, 0.2 mM ThDP, 0.2 mM CoA, 2 mM $MgSO_4$. The reactions also contained 0.1 mg/ml glycerol dehydrogenase to further reduce the dihydroxyacetone product into glycerol through the oxidation of NADH to NAD. Concentrations of formolase (FLS) variant r4b and formate were varied as follows: A) 100 μM FLS+100 mM formate; B) 50 μM FLS+100 mM formate; C) 25 μM FLS+100 mM formate; D) 0 μM FLS+0 mM formate; E) 100 μM FLS+0 mM formate; F) 50 μM FLS+0 mM formate; G) 25 μM FLS+0 mM formate; H) 0 μM FLS+0 mM formate. The consumption of NADH was monitored spectrophometrically at 340 nm. The standard extinction coefficient for NADH of 6220 $M^{-1}$ $cm^{-1}$ was used to convert the absorbance into concentrations. The results are illustrated in FIG. 8.

While illustrative embodiments have been illustrated and described, it will be appreciated that various changes can be made therein without departing from the spirit and scope of the invention.

---

The embodiments of the invention in which an exclusive property or privilege is claimed are defined as follows:

1. A method for converting formaldehyde to dihydroxyacetone, comprising contacting formaldehyde with a thiamine diphosphate cofactor and a polypeptide comprising a motif capable of forming hydrogen bonds with the thiamine diphosphate cofactor, wherein the polypeptide comprises a sequence with at least 80% identity to the benzaldehyde lyase sequence set forth in SEQ ID NO:2;

wherein the motif comprises a histidine residue in a first position corresponding to amino acid residue position 29 of SEQ ID NO:2, an asparagine or a glutamine residue in a second position corresponding to amino acid residue position 113 of SEQ ID NO:2, and a glutamic acid or an aspartic acid residue in a third position corresponding to amino acid residue position 50 of SEQ ID NO:2;

wherein upon association with the thiamine diphosphate cofactor, the cofactor pyrimidine N1 is hydrogen bonded to the acid side chain of the glutamic acid residue or the acid side chain of the aspartic acid residue of the motif; and wherein the histidine N1 and the amide side chain of the asparagine residue or the amide side chain of the glutamine residue are capable of making a water-mediated hydrogen bond with the formaldehyde substrate and/or dihydroxyacetone product.

2. The method of claim 1, wherein the motif comprises at least one amino acid substitution corresponding to the substitutions selected from the group consisting of A394G, A480W, G419N, A28S, and A28I, with reference to the amino acid sequence set forth in SEQ ID NO:2.

3. The method of claim 2, wherein the motif comprises the amino acid substitutions corresponding to A394G and A480W, with reference to the amino acid sequence set forth in SEQ ID NO:2.

4. The method of claim 1, wherein the motif comprises at least three amino acid substitutions corresponding to the substitutions selected from the group consisting of A394G, A480W, G419N, A28S, and A28I, with reference to the amino acid sequence set forth in SEQ ID NO:2.

5. The method of claim 4, wherein the polypeptide comprises an amino acid sequence with at least 80% identity to the sequence set forth in SEQ ID NOS:4, 5, 6, or 7, provided said polypeptide has at least 80% identity to the sequence set forth in SEQ ID NO:2.

6. The method of claim 3, wherein the motif further comprises the amino acid substitutions corresponding to G419N and one of A28S and A28I, with reference to the amino acid sequence set forth in SEQ ID NO:2.

7. The method of claim 6, wherein the polypeptide comprises an amino acid sequence with at least 80% identity to the sequence set forth in SEQ ID NO:8 or SEQ ID NO:9, provided said polypeptide has at least 80% identity to the sequence set forth in SEQ ID NO:2.

8. An engineered polypeptide to convert formaldehyde to dihydroxyacetone, comprising a motif capable of forming hydrogen bonds with a thiamine diphosphate cofactor, wherein the polypeptide comprises a sequence with at least 80% identity to the benzaldehyde lyase sequence set forth in SEQ ID NO:2;

wherein the motif comprises a histidine residue in a first position corresponding to amino acid residue position 29 of SEQ ID NO:2, an asparagine or a glutamine residue in a second position corresponding to amino acid residue position 113 of SEQ ID NO:2, and a glutamic acid or an aspartic acid residue in a third position corresponding to amino acid residue position 50 of SEQ ID NO:2, and the motif further comprises at least one amino acid substitution corresponding to the substitutions selected from the group consisting of A394G, A480W, G419N, and A28I, with reference to the amino acid sequence set forth in SEQ ID NO:2;

wherein upon association with the thiamine diphosphate cofactor, the cofactor pyrimidine N1 is hydrogen bonded to the acid side chain of the glutamic acid residue or the acid side chain of the aspartic acid residue of the motif; and wherein the histidine N1 and the amide side chain of the asparagine residue or the amide side chain of the glutamine residue are capable of making a water-mediated hydrogen bond with the formaldehyde substrate and/or dihydroxyacetone product.

9. The engineered polypeptide of claim 8, wherein the motif further comprises the amino acid substitution corresponding to A28S, with reference to the amino acid sequence set forth in SEQ ID NO:2.

10. The engineered polypeptide of claim 8, wherein the motif comprises the amino acid substitutions corresponding to A394G and A480W, with reference to the amino acid sequence set forth in SEQ ID NO:2.

11. The engineered polypeptide of claim 8, wherein the motif comprises at least three amino acid substitutions corresponding to the substitutions selected from the group consisting of A394G, A480W, G419N, A28S, and A28I, with reference to the amino acid sequence set forth in SEQ ID NO:2.

12. The engineered polypeptide of claim 11, wherein the polypeptide comprises an amino acid sequence with at least 80% identity to the sequence set forth in SEQ ID NOS:4, 5, 6, or 7, provided said polypeptide has at least 80% identity to the sequence set forth in SEQ ID NO:2.

13. The engineered polypeptide of claim 10, wherein the motif further comprises the amino acid substitutions G419N and one of A28S and A28I, with reference to the amino acid sequence set forth in SEQ ID NO:2.

14. The engineered polypeptide of claim 13, wherein the polypeptide comprises an amino acid sequence with 80% identity to the sequence set forth in SEQ ID NO:8 or SEQ ID NO:9, provided said polypeptide has at least 80% identity to the sequence set forth in SEQ ID NO:2.

15. The engineered polypeptide of claim 8, wherein the motif, in association with the thiamine diphosphate cofactor, can convert formaldehyde to dihydroxyacetone with a $k_{cat}/K_m$ constant of at least $0.2\,M^{-1}\,s^{-1}$ under conditions including a buffer with 50 mM potassium phosphate, 0.2 mM thiamine diphosphate, and 2 mM $MgSO_4$, and at pH 8.0 and 25° C.

16. A nucleic acid encoding the engineered polypeptide of claim 8.

17. A vector comprising the nucleic acid of claim 16.

18. A cell transformed with the nucleic acid of claim 16.

19. A method for converting formaldehyde to dihydroxyacetone, comprising contacting formaldehyde with the engineered polypeptide of claim 8.

* * * * *